United States Patent
Jovanovic et al.

(10) Patent No.: US 8,273,245 B2
(45) Date of Patent: *Sep. 25, 2012

(54) MICROFLUIDIC DEVICES, PARTICULARLY FILTRATION DEVICES COMPRISING POLYMERIC MEMBRANES, AND METHODS FOR THEIR MANUFACTURE AND USE

(75) Inventors: Goran Nadezda Jovanovic, Corvallis, OR (US); Sundar V. Atre, New York, NY (US); Brian Kevin Paul, Corvallis, OR (US); Vincent Thomas Remcho, Corvallis, OR (US); Chih-hung Chang, Corvallis, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/292,903

(22) Filed: Nov. 9, 2011

(65) Prior Publication Data
US 2012/0074062 A1     Mar. 29, 2012

Related U.S. Application Data

(63) Continuation of application No. 13/068,037, filed on Apr. 29, 2011, which is a continuation of application No. 11/243,937, filed on Oct. 4, 2005, now Pat. No. 7,955,504.

(60) Provisional application No. 60/616,877, filed on Oct. 6, 2004.

(51) Int. Cl.
   *B01D 63/00*     (2006.01)
   *B01D 61/00*     (2006.01)
   *C02F 1/44*     (2006.01)

(52) U.S. Cl. ............. 210/321.71; 210/645; 210/500.29; 210/500.41

(58) Field of Classification Search .................... None
See application file for complete search history.

(56) References Cited

U.S. PATENT DOCUMENTS
3,356,360 A    12/1967   Ward
(Continued)

FOREIGN PATENT DOCUMENTS
EP    0 324 922    7/1989
(Continued)

OTHER PUBLICATIONS

Allis and Spencer, "16: Nanostructural Architectures from Molecular Building Blocks," *Handbook of Nanoscience, Engineering, and Technology*, pp. 16-1-16-32, 2003.

(Continued)

*Primary Examiner* — Krishnan S Menon
*Assistant Examiner* — Katherine Zalasky
(74) *Attorney, Agent, or Firm* — Klarquist Sparkman, LLP

(57) ABSTRACT

The present disclosure describes devices useful for microscale fluid purification, separation, and synthesis. Such devices generally comprise a fluid membrane that separates two or more fluids flowing through plural microchannels operatively associated with the membrane. Often, the membrane is a semipermeable membrane, such as might be used with a filtration device, such as a dialyzer. Devices of the present invention can be combined with other microscale devices to make systems. For example, the devices may be coupled with one or more microchemical microfactories, one or more micromixers, one or more microheaters, etc. Examples of devices made according to the present invention included an oxygenator, a dialyzer, microheat exchangers, etc.

2 Claims, 31 Drawing Sheets
(27 of 31 Drawing Sheet(s) Filed in Color)

U.S. PATENT DOCUMENTS

| | | | |
|---|---|---|---|
| 3,695,445 A | 10/1972 | Esmond |
| 3,762,032 A | 10/1973 | Bowling et al. |
| 3,809,309 A | 5/1974 | Batista |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,204,628 A | 5/1980 | Houston et al. |
| 4,310,416 A | 1/1982 | Tanaka et al. |
| 4,624,784 A | 11/1986 | Lefebvre |
| 4,647,748 A | 3/1987 | Glassman |
| 4,689,108 A | 8/1987 | Barry, Jr. et al. |
| 4,756,835 A | 7/1988 | Wilson |
| 4,770,787 A | 9/1988 | Heath |
| 4,827,430 A | 5/1989 | Aid |
| 4,869,421 A | 9/1989 | Norris et al. |
| 4,875,619 A | 10/1989 | Anderson et al. |
| 5,087,930 A | 2/1992 | Roy et al. |
| 5,094,749 A | 3/1992 | Seita et al. |
| 5,147,605 A | 9/1992 | Tatsuno et al. |
| 5,232,145 A | 8/1993 | Alley et al. |
| 5,313,023 A | 5/1994 | Johnson |
| 5,316,676 A | 5/1994 | Drori |
| 5,344,392 A | 9/1994 | Senninger et al. |
| 5,385,623 A | 1/1995 | Diaz |
| 5,469,264 A | 11/1995 | Shigemori |
| 5,534,328 A | 7/1996 | Ashmead et al. |
| 5,571,754 A | 11/1996 | Bertin et al. |
| 5,580,523 A | 12/1996 | Bard |
| 5,593,581 A | 1/1997 | Lescoche |
| 5,595,712 A | 1/1997 | Harbster et al. |
| 5,610,645 A | 3/1997 | Moore et al. |
| 5,611,214 A | 3/1997 | Wegeng et al. |
| 5,648,684 A | 7/1997 | Bertin et al. |
| 5,689,966 A | 11/1997 | Zess et al. |
| 5,749,226 A | 5/1998 | Bowman et al. |
| 5,769,985 A | 6/1998 | Kawakami et al. |
| 5,779,833 A | 7/1998 | Cawley et al. |
| 5,811,062 A | 9/1998 | Wegeng et al. |
| 5,813,235 A | 9/1998 | Peterson |
| 5,868,930 A | 2/1999 | Kopf |
| 5,885,456 A | 3/1999 | Charkoudian et al. |
| 5,921,678 A | 7/1999 | Desai et al. |
| 5,932,940 A | 8/1999 | Epstein et al. |
| 5,974,867 A | 11/1999 | Forster et al. |
| 5,985,068 A | 11/1999 | Kawakami et al. |
| 6,024,276 A | 2/2000 | Hirata et al. |
| 6,048,432 A | 4/2000 | Ecer |
| 6,082,891 A | 7/2000 | Schubert et al. |
| 6,100,463 A | 8/2000 | Ladd et al. |
| 6,109,994 A | 8/2000 | Cho et al. |
| 6,121,539 A | 9/2000 | Johnson et al. |
| 6,123,798 A | 9/2000 | Gandhi et al. |
| 6,126,723 A | 10/2000 | Drost et al. |
| 6,129,973 A | 10/2000 | Martin et al. |
| 6,143,247 A | 11/2000 | Sheppard et al. |
| 6,148,635 A | 11/2000 | Beebe et al. |
| 6,167,910 B1 | 1/2001 | Chow |
| 6,192,596 B1 | 2/2001 | Bennett et al. |
| 6,202,312 B1 | 3/2001 | Rando |
| 6,212,333 B1 | 4/2001 | Olk et al. |
| 6,225,497 B1 | 5/2001 | Becker et al. |
| 6,329,139 B1 | 12/2001 | Nova et al. |
| 6,334,301 B1 | 1/2002 | Otsap et al. |
| 6,352,577 B1 | 3/2002 | Martin et al. |
| 6,357,332 B1 | 3/2002 | Vecchio |
| 6,368,505 B1 | 4/2002 | Grummert et al. |
| 6,375,871 B1 | 4/2002 | Bentsen et al. |
| 6,477,058 B1 | 11/2002 | Leubs et al. |
| 6,488,872 B1 | 12/2002 | Beebe et al. |
| 6,490,812 B1 | 12/2002 | Bennett et al. |
| 6,514,412 B1 | 2/2003 | Insley et al. |
| 6,533,840 B2 | 3/2003 | Martin et al. |
| 6,537,506 B1 | 3/2003 | Schwalbe et al. |
| 6,607,644 B1 | 8/2003 | Apffel, Jr. |
| 6,616,877 B2 | 9/2003 | Close et al. |
| 6,616,909 B1 | 9/2003 | Tonkovich et al. |
| 6,623,860 B2 | 9/2003 | Hu et al. |
| 6,635,226 B1 | 10/2003 | Tso et al. |
| 6,652,627 B1 | 11/2003 | Tonkovich et al. |
| 6,654,660 B1 | 11/2003 | Singh et al. |
| 6,656,315 B2 | 12/2003 | Sallavanti et al. |
| 6,666,909 B1 | 12/2003 | TeGrotenhuis et al. |
| 6,672,502 B1 | 1/2004 | Paul et al. |
| 6,676,835 B2 | 1/2004 | O'Connor et al. |
| 6,688,381 B2 | 2/2004 | Pence et al. |
| 6,737,026 B1 | 5/2004 | Bergh et al. |
| 6,744,038 B2 | 6/2004 | Wang et al. |
| 6,749,814 B1 | 6/2004 | Bergh et al. |
| 6,793,831 B1 | 9/2004 | Paul et al. |
| 6,797,056 B2 | 9/2004 | David |
| 6,814,859 B2 | 11/2004 | Koehler et al. |
| 6,838,156 B1 | 1/2005 | Neyer et al. |
| 6,852,231 B2 | 2/2005 | Ivansons et al. |
| 6,863,867 B2 | 3/2005 | Bussche et al. |
| 6,892,781 B2 | 5/2005 | McHerron et al. |
| 6,903,332 B2 | 6/2005 | Weiss et al. |
| 6,911,262 B2 | 6/2005 | Sallavanti et al. |
| 6,913,877 B1 | 7/2005 | Chaplen et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,014,705 B2 | 3/2006 | David |
| 7,094,345 B2 | 8/2006 | Gilbert et al. |
| 7,097,800 B2 | 8/2006 | Vigna et al. |
| 7,118,920 B2 | 10/2006 | Brophy et al. |
| 7,122,156 B2 | 10/2006 | Bergh et al. |
| 7,125,540 B1 | 10/2006 | Wegeng et al. |
| 7,150,815 B2 | 12/2006 | Ashmead et al. |
| 7,211,442 B2 | 5/2007 | Gilbert et |
| 7,264,723 B2 | 9/2007 | Sing et al. |
| 7,279,134 B2 | 10/2007 | Chan et al. |
| 7,378,280 B2 | 5/2008 | Quake et al. |
| 7,501,101 B2 | 3/2009 | Wegeng et al. |
| 7,507,380 B2 | 3/2009 | Chang et al. |
| 7,534,315 B1 | 5/2009 | Singh et al. |
| 2002/0045265 A1 | 4/2002 | Bergh et al. |
| 2002/0108869 A1 | 8/2002 | Savtchenko et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0156991 A1 | 8/2003 | Halas et al. |
| 2003/0168590 A1 | 9/2003 | Weiss et al. |
| 2003/0183345 A1 | 10/2003 | Soberay |
| 2003/0221777 A1 | 12/2003 | McHerron et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0020286 A1 | 2/2004 | Blakely |
| 2004/0022691 A1 | 2/2004 | Allen et al. |
| 2004/0035452 A1 | 2/2004 | Ma |
| 2004/0072278 A1 | 4/2004 | Chou et al. |
| 2004/0084370 A1 | 5/2004 | Singh et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0208751 A1 | 10/2004 | Lazar et al. |
| 2004/0256230 A1 | 12/2004 | Yager et al. |
| 2005/0007748 A1 | 1/2005 | Callahan et al. |
| 2005/0074834 A1 | 4/2005 | Chaplen et al. |
| 2005/0126211 A1 | 6/2005 | Drost et al. |
| 2005/0129580 A1 | 6/2005 | Swinehart et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2005/0220681 A1 | 10/2005 | Chang et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |

| 2007/0131403 | A1 | 6/2007 | Vetrovec et al. |
| 2007/0184576 | A1 | 8/2007 | Chang et al. |
| 2007/0215644 | A1 | 9/2007 | Otis et al. |
| 2007/0278155 | A1 | 12/2007 | Lo et al. |
| 2008/0006040 | A1 | 1/2008 | Peterson et al. |
| 2008/0009780 | A1 | 1/2008 | Leonard et al. |
| 2008/0093298 | A1 | 4/2008 | Browning et al. |
| 2008/0108122 | A1 | 5/2008 | Paul et al. |
| 2009/0165366 | A1 | 7/2009 | Jovanovic et al. |
| 2009/0211977 | A1 | 8/2009 | Miller |

FOREIGN PATENT DOCUMENTS

| GB | 1 289 738 | 9/1972 |
| JP | S55-14045 | 1/1980 |
| JP | S59-58002 | 10/1982 |
| WO | WO 02/40874 | 5/2002 |
| WO | WO 02/076529 | 10/2002 |
| WO | WO 2005/045894 | 5/2005 |
| WO | WO 2006/042079 | 4/2006 |

OTHER PUBLICATIONS

Alm, "Diffusion Bonding—Methods and Applications: Part I—Terminology," Systems Group of TRW Inc., *Adhesives Age*, pp. 28-32, Jul. 1970.

Alman et al., "Processing, Structure and Properties of Aluminum-Aluminide Layered Sheet Composites," *Light Weight Alloys for Aerospace Applications III*, The Minerals, Metals & Materials Society, pp. 531-544, 1995.

Alman et al., "Intermetallic Sheets Synthesized from Elemental Ti, Al and Nb Foils," *Metallurgical and Materials Transactions*, 26A:2759-2762, Oct. 1995.

Alman et al., "Fabrication, Structure and Properties of Aluminum-Aluminide Layered Composites," *Materials Research Society Symp. Proc.*, 434:255-260, 1996.

Alman et al., Fabrication of NiAl Intermetallic Reactors for Microtechnology-Based Energy Chemical Systems (MECS), *Transactions of NAMRI/SME*, XXIX:453-459, 2001.

Anglès et al., "Plasticized starch/Tunicin Whiskers Nanocomposite Materials. 2. Mechanical behavior," *Macromolecules*, 34, pp. 2921-2931, 2001.

Battezzati et al., "Solid State Reaction in Al/Ni Alternate Foils Induced by Cold Rolling and Annealing," *Acta Mater.*, 47:1901-1914, 1999.

Battista, "Chapter Two: Microcrystalline Celluloses," *Microcrystal Polymer Science*, McGraw-Hill, New York, NY, pp. 17-57, 1975.

Benson et al., "Process Miniaturization—A Route to Total Environmental Acceptability?" *Trans. IchemE*, 71(Part A):160-168, 1993.

Bower et al., "Aligned Wafer Bonding: A Key to Three Dimensional Microstructures," *Journal of Electronic Materials*, 20:383-387, 1991.

Chazeau et al., "Mechanical behaviour above $T_g$ of a plasticised PVC reinforced with cellulose whiskers; a SANS structural study," *Polymer*, vol. 40, pp. 5333-5344, 1999.

Colgan, "A Review of Thin-Film Aluminide Formation," *Material Science Reports* 5:1-44, North-Holland, Jan. 1990.

Cuta et al., "Fabrication and testing of microchannel heat exchangers," *SPIE Conf.*, 2640:152-160, 1995.

D'Heurle, "Reactive Diffusion in a Prototype System: Nickel-Aluminum I: Non-Constant Diffusion Coefficient," *Thin Solid Films*, 215:19-25, 1992.

de Souza Lima et al., "Rodlike Cellulose Microcrystals: Structure, Properties, and Applications," *Macromolecular Rapid Communications*, vol. 25, pp. 771-787, 2004.

Deevi et al., "Processing, Properties and Applications of Nickel and Iron Aluminides," *Progress in Materials Science*, 42:177-192, 1997.

Demura et al., "Ductile Thin Foil of $Ni_3Al$," *Mechanical Properties of Structural Films*, 11-12:248-261, 2000.

Demura et al., "Fabrication of $Ni_3Al$ Thin Foil by Cold-Rolling," *Intermetallics*, 9:157-167, 2001.

Derby et al., "Theoretical Model for Diffusion Bonding," *Metal Science*, 16:49-56, Jan. 1982.

Dunford et al., "Diffusion Bonding of Al-Li Alloys," *Materials Science and Technology*, 8:385-398, May 1992.

Duszczyk et al., "The Characteristics of the Diffusion Between the As-Reaction-Formed $Ni_3Al$ Intermetallic Compound and Pure Nickel for Interfacial Bonding," *Journal of Materials Science Letters*, 18:111-113, 1999.

Ehrfeld et al., "Characterization of mixing in micromixers by a test reaction: Single mixing units and mixer arrays," *Ind. Eng. Chem. Res.* 38(3):1075, 1999.

Esposito, *Fluid Power with Applications*, Prentice Hall, pp. 380-381, 1988.

Favier et al., "Nanocomposite Materials from Latex and Cellulose Whiskers," *Polymers for Advanced Technologies* 6:351-355, 1995.

Favier et al., "Mechanical Percolation in Cellulose Whisker Nanocomposites," *Polymer Engineering and Science*, vol. 37, pp. 1732-1739, 1997.

Fischer et al., "Manufacturing of Aluminum Nitride Heat Exchangers by Ceramic Injection Molding," *Ceramic Engineering and Science Proceedings*, 20(4):595-602, 1999.

Garmong et al., "Attainment of Full Interfacial Contact During Diffusion Bonding," *Metallurgical Transactions*, 6A:1269-1279, Jun. 1975.

George et al., "Ordered Intermetallics," *Annu. Rev. Mater. Sci.*, 24:409-451, 1994.

Glatz et al., "Diffusion Bonding of Intermetallic Ti-47Al-2Cr-0-2Si Sheet Material and Mechanical Properties of Joints at Room Temperature and Elevated Temperatures," *Intermetallics*, 5:415-423, Sep. 1997.

Goldberg, "Narrow Channel Forced Air Heat Sink," *IEEE Transactions on Components, Hybrids, and Manufacturing Technology*, CHMT-7(1):154-159, Mar. 1984.

Grunert et al., "Progress in the Development of Cellulose Reinforced Nanocomposites," *Polymeric Materials: Science and Engineering*, Abstracts of papers, Abstract No. 126, 2000.

Krause et al., "Microchannel coolers for high power laser diodes in copper technology," *Proc. SPIE*, 2148:351-385, 1994.

Ling et al., "Passive Alignment and its Application in Multi-level X-ray Lithography," *Materials and Device Characterization in Micromachining III, Proceedings of SPIE*, 4175:43-49, 2000.

Little, "Microminiature Refrigerators for Joule-Thomson Cooling of Electronic Chips and Devices," *Advances in Cryogenic Engineering*, 35:1325-1333, 1990.

Liu et al., "Ordered Intermetallic Alloys, Part I: Nickel and Iron Aluminites," *Journal of Minerals, Metals, and Materials Society*, 45(5):38-44, May 1993.

Lopez et al., "Microstructural analysis of steel-nickel alloy clad interfaces," *Mat. Sci. and Tech.*, pp. 45-55, Jan. 1996.

Martin et al., "Microchannel heat exchangers for advanced climate control," *Proc. SPIE*, 2639:82-88, 1995.

Martin et al., "Microfabrication methods for microchannel reactors and separations systems," *Pacific Northwest National Laboratory*, 8 pages, 1997.

Martin et al., "Microfabrication Methods for Microchannel Reactors and Separations Systems," *Chem. Eng. Comm.*, 173:245-254, 1999.

Matson, "Laser micromachined microchannel solvent separator," *SPIE*, 3223:253-259, 1997.

Matson et al., "Fabrication of Microchannel Chemical Reactors Using a Metal Lamination Process," *Proc. IMRET3*, 10 pages, Frankfurt, Germany, Apr. 1999.

Michaelson et al., "The Early Stages of Solid-State Reactions in Ni/Al Multilayer Films," *J. Appl. Phys.*, 80(12):6689-6698, Dec. 1996.

Moore et al., "Diffusion Brazing NiAl with Self-Generated Filler Metal," Materials Research Society, *Mat. Res. Soc. Symp. Proc.*, 288:1173-1178, 1993.

Morin et al., "Nanocomposites of Chitin Whiskers from *Riftia* Tubes and Poly(caprolactone)," *Macromolecules*, vol. 35, pp. 2190-2199, 2002.

Nakamura et al., "Research on Pressure Welding Conditions of Various Work Metals (Effects of Contact Pressure, Surface Expansion Ratio and Temperature)," *JSME International Journal*, Series III 31(3):612-617, 1988.

Nakao et al., "Diffusion Bonding of Intermetallic Compound TiAl," *ISIJ International*, 31(10):1260-1266, 1991.

NASA, "National Space Transportation System Shuttle Reference Manual," p. 8, located at www.ksc.nasa.gov/shuttle/technology/sts-newsref/sts-oms.html, 1988.
Oddy et al., "Electrokinetic Instability Micromixing," *Anal. Chem.*, 73:5822-5832, 2001.
Orhan et al., "A New Model for Diffusion Bonding and its Application to Duplex Alloys," *Materials Science and Engineering*, A271:458-468, 1999.
Orts et al., "Effect of Fiber Source on Cellulose Reinforced Polymer Nanocomposites," Annual Technical Conference—Society of Plastics Engineers, $62^{nd}$, pp. 2427-2431, (2 pages) 2004.
Paillet et al., "Chitin Whisker Reinforced Thermoplastic Nanocomposites," *Macromolecules*, vol. 34, No. 19, pp. 6527-6530, 2001.
Paransky et al., "Kinetics of Two-Phase Layer Growth During Reactive Diffusion," *Materials Science and Engineering*, A270: 231-236, 1999.
Paul et al., "Microlamination for Microtechnology-based Energy, Chemical, and Biological Systems," *ASME IMECE* 39:45-52, Nashville, Tennessee, Nov. 15-20, 1999.
Paul et al., "Intermetallic Microlamination for High-Temperature Microreactors," 4th Int. Conf. Microreaction Tech., Atlanta, Georgia, pp. 236-243, American Institute of Chemical Engineers [AIChE], Mar. 5-9, 2000.
Paul et al., "Intermetallic Microlamination for High-Temperature Microreactors," *4th Int. Con. Microreaction Tech.*, Mar. 2000.
Paul et al., "Limits on Aspect Ratio in Two-fluid Micro-scale Heat Exchangers," *Transactions of NAMRI XXIX*, Gainesville, Florida, 2001.
Paul et al., "An Evaluation of Two Methods for Producing Intermetallic Microchannels," *Proceedings of IMEC*, pp. 261-266, ASME International Mechanical Engineering Congress of Exposition, New Orleans, Louisiana, Nov. 17-22, 2002.
Paul et al., "Understanding Limits on Fin Aspect Ratios in Counterflow Microchannel Arrays Produced by Diffusion Bonding," *J. Manuf. Sci. Eng.*, 128(4):977, Nov. 2006.
Peterson, "Size Limits for Regenerative Heat Engines," *Microscale Thermophysical Engineering*, 2:121-131, 1998.
Peterson et al.., "Numerical Modeling of Conduction Effects in Microscale Counterflow Heat Exchangers," *Microscale Thermophysical Engineering*, 3:17-30, 1999.
Philibert, "Reactive Diffusion in Thin Films," *Applied Surface Sciences*, 53:74-81, North-Holland, 1991.
Pilling, "The Kinetics of Isostatic Diffusion Bonding in Superplastic Materials," *Materials Science and Engineering*, 100:137-144, 1988.
Pilling, "On the Modeling of Diffusion Bonding in Materials: Superplastic Super Alpha-2," *Materials Science and Engineering* A205:72-78, 1996.
Pluess, "Application of Controlled Thermal Expansion in Diffusion Bonding for the High-Volume Microlamination of MECS Devices," Thesis (MS)—Oregon State University, 2004.
Grunert et al., "Cellulose Nanocrystal Reinforced Cellulose Acetate Butyrate Nanocomposites," *Polymeric Materials: Science and Engineering*, vol. 86, pp. 367-368, 2002.
Haas et al., "Fabrication and Performance of MMW and SMMW Platelet Horn Arrays," *Intl. J. Infrared and Millimeter Waves*, 14(11):2289-2293, 1993.
Haas, "Further development of MMW and SMMW platelet feed horn arrays," *Astron. Soc. Pac. Conf. Ser.*, 75:99-105, 1995.
Herschberg, "Manufacturing Technology of the Tektronix Digital Ink Jet Head," *SPSE $3^{rd}$ International Congress on Advances in Non-Impact Printing Technologies, Journal of Imaging Technology*, 14:124-128, 1998.
Hessel et al., "High Temperature HCN Generation in an Integrated Microreaction System," *Proc. IMRET3*, Frankfurt, Germany, pp. 151-164, Apr. 1999.
Hill et al., "Modelling Solid-State Diffusion Bonding," *Acta Metal. Mater.*, 37(9):2425-2537, 1989.
Humpston et al., "Principles in Soldering and Brazing, 4.4.2. Diffusion Soldering and Brazing," *ASM International*, pp. 128-143, 1993.
Islam et al., "Effect of Surface Finish and Sheet Thickness on Isostatic Diffusion Bonding of Superplastic Ti-6Al-4V," *Materials Science and Technology*, 13:1045-1050, Dec. 1997.

Islam et al., "Isostatic Diffusion Bonding of a Microduplex Stainless Steel," *Scripta Materialia*, 38(8):1187-1193, 1998.
Jacobson et al., "Diffusion Soldering," *Soldering and Surface Mount Technology*, Chap. 10, pp. 27-32, Feb. 1992.
Kao et al., "A Theoretical Analysis for the Formation of Periodic Layered Structure in Ternary Diffusion Couples Involving a Displacement Type of Reaction," *Acta. Metal. Mater.*, 41(12):3463-3472, 1993.
Khan et al., "Transient liquid phase diffusion bonding and associated recrystalization phenomenon when joining ODS ferritic superalloys," *J Mat. Sci.*, 31:2937-2943, Jun. 1996.
Kleiner, "High Performance Forced Air Cooling Scheme Employing Microchannel Heat Exchangers," *IEEE Transactions on Components, Packaging, and Manufacturing Technology*, 18(4):795-804, Dec. 1995.
Knight, "Optimal Thermal Design of Air Cooled Forced Convection Finned Heat Sinks—Environmental Verification," *IEEE Transactions on Components, Hybrids, and Manufacturing Technology*, 15:754-760, 1992.
Koeneman et al., "Feasibility of Micro Power Supplies for MEMS," *J. MicroElectoMechanical Sys*, 6(4):355-362, 1997.
Pluess et al., "Application of Controlled Thermal Expansion in Microlamination for the Economical Production of Bulk Microchannel Systems," *Chem. Engr. Comm.*, 194:1259-1270, 2007.
Porter et al., "Cost Drivers in Microlamination Based on a High-Volume Production System Design," *Proceedings of IMECE 2002, ASME International Mechanical Engineering Congress & Exposition*, Nov. 17-22, 2002, New Orleans, Louisiana.
PowerPoint slides presented at $4^{th}$ International Conference of Microreaction Technology, Atlanta, Georgia, Mar. 5-9, 2000.
Raviprasad et al.., "Layered Structures Produced by Rolling Dissimilar Metals," *Journal of Materials Science Letters*, 15:511-514, 1996.
Revol et al., "Cellulose-based Chiral Nematic Structures," in *Cellulosics: Chemical, Biochemical and Material Aspects*, Eds J.F. Kennedy, G.O. Phillips and P.A. Williams, Ellis Horwood, New York, pp. 115-122, 1993.
Ridley et al., "Isostatic diffusion bonding of microduplex stainless steel," *Mat. Sci. and Tech.*, 8: 791-795, Sep. 1992.
Robertson et al., "In Situ Interferometric Alignment Systems for the Assembly of Microchannel Relay Systems," *Applied Optics*, 36:9253-9260, 1997.
Rode et al.., "Self-Aligned Positioning of Microoptical Components by Precision Prismatic Grooves Impressed in Metal," *IEEE Journal of Microelectromechanical Systems*, 8:58-64, Mar. 1999.
Ruiz et al., "Processing and characterization of new thermoset nanocomposites based on cellulose whiskers," *Composite Interfaces*, vol. 7, No. 2, pp. 117-131, 2000.
Schwab et al., "Molecular Rods. 1. Simple Axial Rods," *Chemical Reviews*, 99(7):1863-1933, 1999.
Sharma et al., "The Application of Surface Mount Technology to Multi-Scale Process Intensification," *ASPE*, pp. 1-4, Oct. 2003.
Spadaccini et al., "Development of a Catalytic Silicon Micro-Combustor for Hydrocarbon-Fueled Power Mems," *The Fifteenth IEEE International Conference on Micro Electro Mechanical Systems*, pp. 228-231, Las Vegas, Nevada, Jan. 20-24, 2002.
Stroock et al., "Chaotic Mixer for Microchannels," *Science*, 295:647-651, 2002.
Strum et al.., "Liquid-Assisted Diffusion Bonding of NiAl," *Advanced Joining Technologies for New Materials II*, Conference Proceedings, pp. 76-88, Mar. 1994.
"Technology Development Through Industrial Partnerships," *Federal Energy Technology Center*, Oct. 1997.
Tour, "Chapter 3: Chemical Synthesis," *Molecular Electronics, Commercial Insights, Chemistry, Devices, Architecture and Programming*, World Scientific, pp. 33-41, Mar. 2003.
Uenishi et al.., "Joining of Intermetallic Compound TiAl by Using Al Filler Metal," *Zeitschrift fur Metallkunde*, 86(4):270-274, 1995.
van Loo et al., "Solid State Diffusion and Reactive Phase Formation," *Solid State Ionics*, 95:95-106, 1997.
Wang et al., "Ni-$Al_2O_3$ and Ni-Al Composite High-Aspect-Ratio Microstructures," *Materials and Device Characterization in Micromachining*, 3512:344-352, 1998.

Wattanutchariaya et al., "Bonding Fixture Tolerances for High-Volume Metal Microlamination Based on Fin Buckling and Lamina Misalignment Behavior," *J. Intl Soc of Precision Engr and Nanotechnology*, 2002.

Wegeng et al., "Energy systems miniaturization technologies, devices, and systems," *Proceedings of the International Symposium on Advanced Energy Conversion Systems and Related Technologies* (RAN95), 8 pages, Dec. 1995.

Wegeng et al., "Chemical system miniaturization," *Proceedings of the AIChE Spring National Meeting*, pp. 1-13, Feb. 1996.

Welding Institute, http://www.twi.co.uk/j32k/protected/band_3/ksab001.html, accessed on Feb. 22, 2008.

Wu et al., "Superplastic Forming/Diffusion Bonding of Laser Surface Melted TiAl Intermetallic Alloy," *Scripta Materialia*, 45:895-899, 2001.

Yussuf et al., "Microwave Welding of Polymeric-Micro fluidic Devices," *Micromec. Microeng.*, 15:1692-1699, 2005.

International Search Report dated Sep. 16, 2010, from International Patent Application No. PCT/US2010/037621.

Chinese State Intellectual Property Office Action dated Feb. 20, 2009, in Chinese Patent Application No. CN 200580041446.8.

U.S. Appl. No. 09/369,679—Office Action dated Jun. 22, 2001.
U.S. Appl. No. 09/369,679—Office Action dated Apr. 11, 2002.
U.S. Appl. No. 09/369,679—Office Action dated Dec. 6, 2002.
U.S. Appl. No. 09/996,621—Office Action dated May 16, 2003.
U.S. Appl. No. 10/576,963—Office Action dated Jan. 29, 2009.
U.S. Appl. No. 10/576,963—Office Action dated Jul. 28, 2009.
U.S. Appl. No. 10/576,963—Office Action dated Jan. 25, 2010.
U.S. Appl. No. 10/803,502—Office Action dated Jun. 6, 2008.
U.S. Appl. No. 10/803,502—Office Action dated Mar. 30, 2009.
U.S. Appl. No. 10/803,502—Office Action dated Oct. 21, 2009.
U.S. Appl. No. 11/086,074—Office Action dated Apr. 1, 2008.
U.S. Appl. No. 11/243,937—Office Action dated Apr. 15, 2009.
U.S. Appl. No. 11/243,937—Office Action dated Sep. 20, 2010.
U.S. Appl. No. 11/490,966—Office Action dated Jul. 21, 2008.
U.S. Appl. No. 11/490,966—Office Action dated Oct. 21, 2008.
U.S. Appl. No. 11/517,731—Office Action dated Jun. 6, 2008.
U.S. Appl. No. 11/517,731—Office Action dated Aug. 29, 2008.
U.S. Appl. No. 11/576,804—Office Action dated Jun. 10, 2010.
U.S. Appl. No. 11/576,804—Notice of Allowance dated Nov. 29, 2010.

Cross - section of ultrasonic packaging technique.

(a)  (b)  (c)

A diagram of (a) a "nanofactory" producing the generalized structure of a dendrimer, (b) a branched architecture[3,65] and (c) a 3-D space filling model.

*Micrographs of (a) 75 µm thick laser-machined polyimide (200X) and (b) 15 µm thick micromolded PDMS (500X) membranes with 5-8 µm pores on 100 µm spacing.*

5 μm diameter posts with height of 65 μm (1:13 aspect ratio) on a silicon wafer

PDMS spin coated onto SU8 micromold

SU8 post

SU8 post coated with PEG (2280X)

MICROFLUIDIC DEVICES, PARTICULARLY FILTRATION DEVICES COMPRISING POLYMERIC MEMBRANES, AND METHODS FOR THEIR MANUFACTURE AND USE

CROSS REFERENCE TO RELATED APPLICATION

This application is a continuation of U.S. patent spplication Ser. No. 13/068,037, filed Apr. 29, 2011, which is a continuation of U.S. patent application Ser. No. 11/243,937, filed Oct. 4, 2005 now U.S. Pat. No. 7,955,504, which claims the benefit of the earlier filing date of U.S. Provisional Application No. 60/616,877, filed on Oct. 6, 2004. The entire disclosures of these prior applications are incorporated herein by reference.

FIELD

The present disclosure concerns microchannel devices having polymer membranes operatively associated therewith, such as purification devices having membranes for filtering fluids, one example being a dialyzer.

BACKGROUND

There are a number of important systems that require fluid purification, particularly liquid purification. Community water systems, for example, obtain water from local sources, such as lakes and rivers, but such water sources often contain impurities, and also may contain bacteria and other microbiological organisms, that can cause disease. Consequently, water from surface sources must be purified before it can be consumed. Water treatment plants typically clean water by taking it through the following processes: (1) aeration; (2) coagulation; (3) sedimentation; (4) filtration; and (5) disinfection. Portable water purification systems would benefit the production of potable water in areas where there are few if any water treatment plants.

Fluid oxygenators also provide an important example of fluid purification. Oxygenator is the main element of the heart-lung machine, which takes over the work of the lungs by adding oxygen to and removing carbon dioxide from the blood. Inside the oxygenator, blood is channelled along capillary membranes. The inner lumen of the fibres is streamed with oxygen or oxygen enriched air. Oxygen diffuses through the microporous membrane into the blood, while carbon dioxide diffuses out of the blood into the gas stream and is thereby removed. Most oxygenators also include a heat exchanger to maintain the correct temperature of the patient's blood. The oxygenated blood is channelled back to the patient.

Another important example of liquid purification is dialysis. The chemical composition of blood must be controlled to perform its essential functions of bringing nutrients and oxygen to the cells of the body, and carrying waste materials away from those cells. Blood contains particles of many different sizes and types, including cells, proteins, dissolved ions, and organic waste products. Some of these particles, including proteins such as hemoglobin, are essential for the body to function properly. Others, such as urea, a waste product from protein metabolism, must be removed from the blood. Otherwise, they accumulate and interfere with normal metabolic processes. Still other particles, including many of the simple ions dissolved in the blood, are required by the body in certain concentrations that must be tightly regulated, especially when the intake of these chemicals varies.

The kidneys are largely responsible for maintaining the chemistry of the blood by removing harmful particles and regulating the blood's ionic concentrations, while keeping the essential particles. Kidneys act like dialysis units for blood, making use of different particle sizes and specially-maintained concentration gradients. Blood passes through membrane-lined tubules of the kidney, analogous to the dialysis tubes used in dialysis units. Particles that can pass through the membrane pass out of the tubules by diffusion, thus separating the particles that remain in the blood from those that will be removed from the blood and excreted.

Kidneys can effectively maintain the body's chemistry as long as at least ten percent of their functional units are working. Damage to the kidneys that causes the functional capacity to drop below this level may cause fatal illness unless an artificial system performs the work of the kidneys. Without artificial kidney dialysis, toxic wastes build up in the blood and tissues, and cannot be filtered out by the ailing kidneys. This condition is known as uremia, which means literally "urine in the blood." Tens of thousands of people currently require kidney dialysis, and the number is growing. Kidney dialysis is intrusive, expensive, and complicated. Patients suffer from current treatment protocols due to extensive side effects. Home dialysis is much preferable to the current practice of having patients treated at dialysis centers. Improved technology is needed, however, to make home dialysis feasible and affordable for patients. Conventional dialysis units are configured as hollow fibers. The membranes are manufactured using spinning technology and generally are about $35\mu$ thick. The membrane is highly porous with the exception of the inner $\sim 1\mu$, which actually performs the separation, retaining blood cells but allowing small molecules to diffuse therethrough. These known dialyzers use membranes typically made of cellulose acetate, cuprophan or polysulfone. Blood is pumped through these fibers, and then back into the patient. The membrane has a molecular weight cut-off that allows most solutes in the blood to pass out of the tubing but retains the proteins and cells. Thus, artificial kidney dialysis uses the same chemical principles that are used naturally in the kidneys to maintain the chemical composition of the blood. Diffusion across semipermeable membranes, polarity, and concentration gradients are central to the dialysis process for both natural and artificial kidneys.

SUMMARY

The present invention is directed to microscale fluid purification, separation, and synthesis devices. Generally, such devices comprise a fluid membrane that separates two or more fluids flowing through plural microchannels operatively associated with the membrane. The fluids can both be liquids, gases, or a liquid and a gas, such as may be used for gas absorption into a liquid. Often, the membrane is a semipermeable membrane, such as might be used with a filtration device, such as a dialyzer.

Devices of the present invention can be combined with other devices to make systems. For example, the devices may be coupled with: one or more microchemical microfactories, such as nanofactories useful for making, amongst other materials, dendrimers; one or more micromixers, such as a micromixer comprising posts positioned to impinge fluid flowing to the microchannels or a micromixer comprising regions of hydrophobic surface and hydrophilic surface; one or more microheaters; etc.

One example of a device made according to the present invention is an oxygenator. For this embodiment, the fluid is a gas, namely oxygen. For oxygenating blood, the liquid component is blood.

Microheat exchangers also can be made using the method described herein.

Particular materials had to be developed for use with certain embodiments of the device disclosed herein. For example, a new composite material was made comprising nanocrystalline cellulose filler and a polysulfone polymeric material. The composite can comprise any suitable amount of nanocrystalline cellulose filler, with likely amounts ranging from greater than zero weight percent nanocrystalline filler to about 10 percent filler, and more likely from about 1 percent to about 5 percent nanocrystalline filler. A dialyzer comprising the composite membrane also is disclosed. One embodiment of the dialyzer comprised a dialyzer membrane comprising nanocrystalline cellulose filler and a polysufone polymeric material, and a microchannel fluidic device fluidly associated with the membrane to provide a blood flow and a dialysate flow adjacent the membrane.

In order to make the nanocrystalline cellulose-polymer composite, a new method was devised for making an organic dispersion of nanocrystalline cellulose. The method comprised first forming an aqueous dispersion of nanocrystalline cellulose. A mixture was then formed comprising the aqueous dispersion and an organic liquid having a boiling point higher than water. The water was then selectively removed to form a second mixture comprising the nanocrystalline cellulose and the organic liquid. Water can be selectively removed by a process similar to distillation, such as by heating the composite mixture to a temperature sufficient to remove the water but not the organic liquid, reducing the pressure sufficient to allow selective water removal, or both. A person of ordinary skill in the art will realize that a number of organic liquids can be used to practice this method. Solely by way of example, and without limitation, the organic liquid may be dimethylformamide, n-methylpyrollidone, tetrahydrofuran, or combinations thereof.

The nanocrystalline cellulose may be prepared from a suitable source, such as a material selected from the group consisting of wood, cotton, *Tunicin*, *Cladophora* sp., *Valonia*, bacteria, chitin, potato starch, and combinations thereof. The nanocrystalline cellulose also may be surface modified to make it more compatible with the polymeric material. The surface modified cellulose may be surface modified by a physical process, such as flame or corona discharge oxidation, or by a chemical process using a material selected, without limitation, from the group consisting of silyl, trimethyl silyl, epoxy, isocyanate, acetate, maleate, sulfate, phosphate, an ester/sulfate mix, anhydrides, and combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Polymer-Filler Composites

Figure 1A:
FIGS. 1A-1C provide AFM images of cellulose nanocrystals, with the top image at 400 nm scale, middle image, a measurement showing a typical length of 191 nm, and the bottom image showing the lowest observed height of 3.7 nm.
Figure 1B:
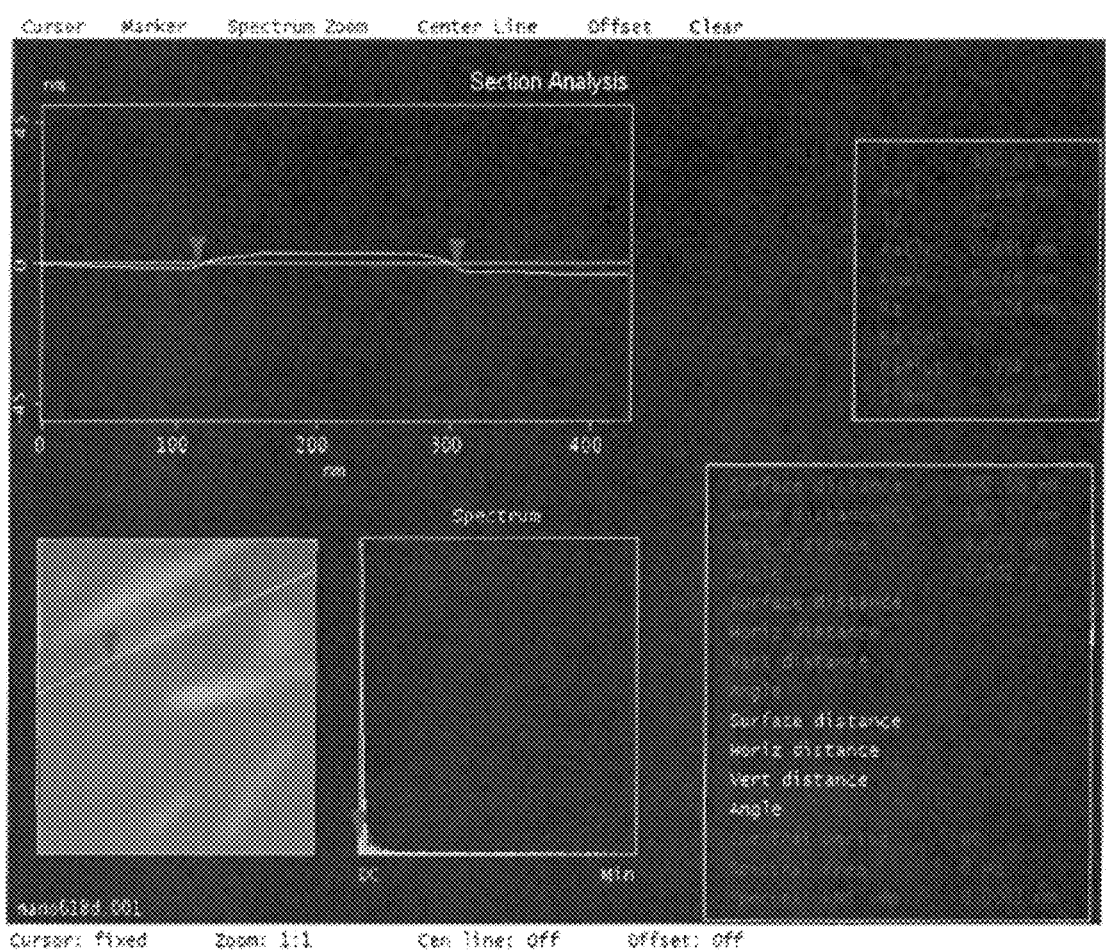
Figure 1C:
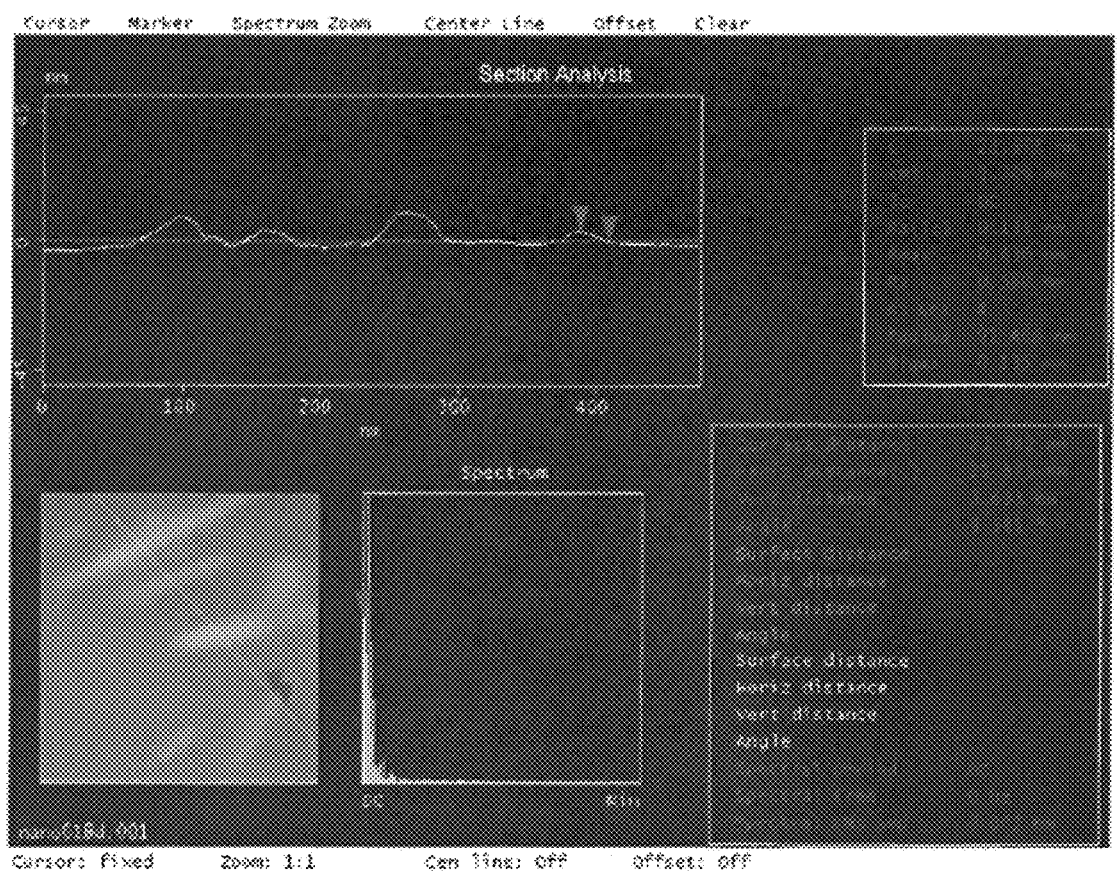

Adding fillers to polymeric systems, such as polysulfone membranes, can improve the performance under certain conditions. Smaller fillers seem to have special advantages. As the size of the filler particles becomes small, the surface area of the filler becomes correspondingly large. The polymer molecules next to the surface are always modified by that surface. Thus, disruptions in the configuration of the polymer chain can occur. This can serve to increase the free volume of the polymer, resulting in greater porosity and enhanced flux across the membrane. Also, shrinking during membrane formation can create small cracks and voids next to the filler particles, which increase permeability and thus overall flux through the membrane. Perhaps surprisingly, this effect does not necessarily result in reduced selectivity. Selectivity probably will be altered in such a situation, but should still be controllable, especially in the case of hemodialysis, where size is the primary selection factor.

Prior to the present disclosure, high-aspect-ratio nanoparticles apparently have not been used as fillers in polysulfone membranes. These materials are long, thin rods that are strong and stiff, and improve the mechanical properties of the membrane. The long, thin rods also can be oriented in the membrane. When oriented parallel to the membrane surface, they enhance the stiffness of the membrane. When oriented perpendicular to the membrane surface the nanoparticles decrease the compressibility of the membrane. Highly compressible membranes typically show poor permeability. The perpendicular orientation also allows for paths of diffusion for the permeate and decreases the time required for small molecules to pass through the membrane. This should increase overall flux, which is highly desirable as it reduces the overall size of the unit required. One embodiment of a disclosed membrane was made using cellulose nanocrystals as a filler for polymeric systems useful for making filters, including without limitation, cellulose acetate, ceprophon or polysulfone.

A. Nanocrystalline Cellulose

Cellulose is the largest volume polymer on earth. It is contained in virtually all plants and is produced by certain bacteria and small sea animals. New uses are still being found for cellulose. One of these is nanocrystalline cellulose (NCC). Cellulose is a semicrystalline polymer, and crystalline portions of the polymer may be liberated by acid hydrolysis. Battista, O. A., 1975. Microcrystal Polymer Science. Microcrystal Polymer Science. McGraw-Hill, New York, N.Y. Revol, J.-F., J. Giasson, J.-X. Guo, S. J. Hanley, B. Harkness, R. H. Marchessault and D. G. Gray, Kennedy, J. F., G. O. Phillips and P. A. Williams, 1993. Cellulose-Based Chiral Nematic Structures. Ellis Horwood Limited 115-122. The size and shape of these crystals varies with their origin. Nanocrystalline cellulose from wood is 3 to 5 nm in width and 20-200 nm long; from *Valonia*, a sea plant, 20 nm in width and 100-2000 nm long; from cotton, 3-7 nm in width and 100-300 nm long; from *Tunicin*, a sea animal, 10 nm in width and 500-2000 nm long.

NCC production technology extends the current industrial production of microcrystalline cellulose (MCC), which was developed in the 1960's and is used for a variety of purposes, mostly in the pharmaceutical and food industries. Almost every aspirin, or other kind of tablet, contains MCC as the drug carrier or as a processing aid. MCC is derived from bleached, dissolving grade wood pulp that has been acid hydrolyzed. Battista, O. A. 1965. Colloidal macromolecular phenomena. American Scientist. 53, 151-173. Under moderate conditions of acid hydrolysis, the cellulose in the pulp is degraded, but the rate at which the degree of polymerization (DP) reduces slows after a certain fiber degradation level occurs. The cellulose degradation proceeds slowly after this point, which is called the level off degree of polymerization (LODP). Here the cellulose consists of a large size distribution of particles, mostly in the micron range. Under the influence of high shear, the particles are further comminuted. It is possible to produce a reasonable (20 to 30% or so, depending upon species and processing method) yield of nanocrystals of cellulose. These are the basic crystal units which exist in the crystalline domains of the cellulose polymer. While there is a large distribution of sizes in the industrial product, the standard deviation of the LODP is relatively small, by biological standards at least. For commercial MCC the LODP is about 230. Moorehead measured the crystallite corresponding to a DP of 297 as 3.7 nm in width, 4.5 nm in thickness, and an average of 150 nm in length (minimum length was 120 nm and maximum 330 nm). Moorehead, F. F. 1950. Text. Res. J. 20, 549. Microcrystalline cellulose is composed primarily of aggregates of the LODP crystallites.

A film prepared from a nanocrystal suspension had a rough density measurement of 1.6±0.1 g/cc, about the same density as the cellulose crystal. The density of crystalline cellulose calculated from X-ray diffraction data is 1.566 g/cc. Films from NCC are transparent and show birefringence, suggesting a high degree of crystal orientation in the film, at least within domains. The oriented nature of the crystals in the film is apparent even in an optical microscope image.

The material properties of nanocrystals have not been measured directly, but estimates for the strength and stiffness of the cellulose are about 134 GPa for stiffness and 7,500 MPa for strength (a theoretical calculation). Marks, R. E., Cell wall mechanics of tracheids. Yale Univ. Press, New Haven, Conn. (1967). Comparisons with other materials are shown in Table 1. The extension to break of NCC is estimated to be only 2% [Marks].

TABLE 1

Comparison of mechanical properties for various materials

| Material | Strength, MPa | Stiffness, GPa |
|---|---|---|
| cellulose crystal | 7500 | 134 |
| Aluminum | 620 | 73 |
| E-glass | 3400 | 72 |
| Steel | 4100 | 207 |
| Graphite | 1700 | 250 |
| Carbon nanotubes | 120,000 | |

Most commonly, cellulose nanocrystals are not prepared from wood, but rather from a variety of biological sources: *Tunicin*, e.g. *Halocynthia roretzi*, a sea animal; *Cladophora* sp. a green algae; *Valonia*, a seaweed; bacteria; chitin; and even potato starch have been used as raw materials for nanocrystal production.

Cellulose nanocrystals have useful reinforcing properties in a variety of polymer systems as indicated by the following: Favier, V. G. Canova, S. Shrivastava and J. Cavaille, Mechanical percolation in cellulose whisker nanocomposites, Polymer Engineering and Science, 37, 1732-1739 (1997); Chazeau, L. J. Y. Cavaille and P. Terech, Mechanical behaviour above Tg of a plasticised PVC reinforced with cellulose whiskers; a SANS structural study. Polymer, 40, 5333-5344 (1999); Cellulose nanocrystals have been investigated as fillers in siloxanes, such as by Grunert, M. and W. Winter, Progress in the development of cellulose reinforced nanocomposites, Polymeric materials, science and engineering (2000). Poly(caprolactone), Morin, A. and A. Dufresne, Nanocomposites of chitin whiskers from *Riftia* tubes and poly(caprolactone), Macromolecules, 35, 2190-2199 (2002); glycerol-plasticized starch, Angles, M. N. and A. Dufresne (2001). Plasticized starch/*tunicin* whiskers nanocomposite materials. 2. Mechanical behavior, Macromolecules. 34, 2921-2931; styrene-butyl acrylate latex, Paillet, M. and A. Dufresne (2001). Chitin whisker reinforced thermoplastic nanocomposites, Macromolecules, 34, 6527-6530; Grunnert, M. and W. Winter, Cellulose nanocrystal reinforced cellulose acetate butyrate nanocomposites, Abstracts of papers, $223^{rd}$ National ACS meeting, Polymeric materials, science and engineering. p. 240 (2002); epoxies, Ruiz, M., J. Cavaille, A. Dufresne, J. Gerard and C. Graillat, Processing and characterization of new thermoset nanocomposites based on cellulose whiskers, Composite Interfaces, 7, 117-131(2000); and thermoplastic starch, Orts, W. J., S. H. Imam, J. Shey, G. M. Glenn, M. K. Inglesby, M. E. Guttman and A. Nguyen, Effect of fiber source on cellulose reinforced polymer nanocomposites, Annual Technical Conference—Society of Plastics Engineers, $62^{nd}$, 2427-2431 (2004).

At very low nanocrystal loadings the composite reaches a percolation threshold. This is the filler level at which the filler particles begin to contact each other and form a three-dimensional network. The modulus builds very rapidly from this point to extremely high values. This percolation effect has been well-studied in regards to electrical conductivity in filled polymer systems. Above the percolation threshold, the shear modulus has been observed to increase by more than three orders of magnitude. This required nanocrystal loadings of only 6%. Favier, V., G. Canova, S. Shrivastava and J. Cavaille. 1997. Mechanical percolation in cellulose whisker nanocomposites. Polymer Engineering and Science. 37, 1732-1739.

Cellulose nanocrystals have not been used extensively in the common thermoplastics, e.g. polyethylene and polypropylene, as they are more expensive than wood flour and not readily available, and they are thermally sensitive at the temperatures commonly used to extrude thermoplastics. Such composites also face the same incompatibility problem inherent in wood-plastic composites because the cellulose tends to agglomerate and the resulting composite is more susceptible to moisture than the neat plastic. This may be addressed, however, by surface modifying the polymeric material.

The interest in nanocrystalline cellulose stems not only from the superior properties of this material, but also from the very high aspect ratios (length divided by width) available (in some cases>500). High-aspect-ratio fillers provide improved polymer-filler composite properties. In addition, they offer the possibility of directionality in the mechanical properties of the composite by aligning the nanocrystals in the desired direction. Another advantage of NCC is its relative uniformity in terms of size and shape. Carbon nanotubes are typically produced in a huge array of diameters and lengths.

B. Making NCC/Organic Liquid Dispersions using a Solvent Exchange Process

New membranes need to be developed for use in filtration devices, such as composite polymer-fiber materials. The incorporation of NCC into polymers without aggregation has been problematic. De Souza Lima, M. M. and R. Borsali, Rodlike cellulose microcrystals: structure, properties, and applications, Macromolecular Rapid Communications. 25, 771-787 (2004). For example, the most advanced research group in the cellulose nanocrystal area, Dr. DuFresne's group at EFPG-INPG in St. Martin D'Heres Cedex, France, used freeze drying then ultrasonication to suspend NCCs (referred to as cellulose whiskers) in dimethylformamide (DMF).

The freeze drying step used in known processes can be eliminated by embodiments of a solvent exchange process disclosed herein. Solvent exchange works well as a process for transferring NCC from an aqueous suspension to an organic liquid suspension. The organic liquid suspension then can be used for subsequent processes utilizing a polymeric material, such as a polysulfone, or potentially a polymeric material precursor. Subsequent coagulation provides a method for membrane formation. This is a potentially enabling concept for a variety of polymer systems.

One embodiment of the method comprises forming an aqueous dispersion of nanocrystalline cellulose. The nanocrystalline cellulose can be made from a source of cellulose by treating the cellulose with an acid, and comminuting the resulting cellulosic material. A mixture is then formed comprising the aqueous dispersion and an organic liquid. A suitable organic liquid for this step can be selected by considering organic liquids in which the NCC can be dispersed, the boiling point of the liquid (higher than water but sufficiently low to allow efficient removal) and other factors that would be understood by a person of ordinary skill in the art, such as cost, availability, etc. By way of example only, organic liquids currently deemed useful include dimethylformamide, n-methylpyrollidone, and combinations thereof The water is then removed, without freeze drying, to form a second mixture comprising the nanocrystalline cellulose and the organic liquid. The water is selectively removed by processes similar to distillation, such as be modifying the pressure and/or temperature to allow selective removal of the aqueous phase.

The second mixture is added to a polymeric material or polymeric material precursor to form a composite mixture. The second mixture is then used as desired. Composite materials have been formed using this technique. For example, an organic-liquid dispersion of NCC has been added to polysulfone. The resulting polymeric composite material was then formed into films. Filtration membranes can be made by forming apertures in the composite material. One method for forming such apertures comprises using a sacrificial liquid that can be removed from the composite film subsequent to its formation, such as by heating, leaving behind pores to form a membrane.

C. Surface Modification

Chemical compatibility is an important issue in composite materials. NCC has the advantage of being easily modified by chemical treatments. Several literature references describe the surface modification of cellulose nanocrystals. See, for example, Ladouce, (2000), who teaches using a variety of agents that react with the cellulose hydroxyl group, primarily silylation, epoxy, and isocyanate compounds; and Winter, who describes acetate, maleate, sulfate, and trimethyl silyl modifications (2001). Successful MCC surface modification without significant degradation of the crystalline structure has been demonstrated by grafting phosphate, an ester (pyromellitic), and an ester/sulfate mix [Kotelnikova, (1993)]. The use of anhydrides as surface modifying agents also is known [Trejo-O'Reilly, (1997)].

D. Thermal Limits

NCC begins to oxidize in air around 130° C. This limits its usefulness and prohibits typical plastic processing in extruders, injection molders, etc. In addition, dispersing dry NCC in molten plastic requires intense shear that would most likely be expensive and degrading to the final composite properties. However, this thermal sensitivity should not be a serious impediment to membrane applications, since they usually use coagulation from solvent as the processing method. Biomedical applications also usually incorporate low temperature processes.

E. Biocompatibility

Cellulose and cellulose derivatives have a long history in the biomedical field. Cellulose acetate is an important polymer for use in dialysis membranes (although in recent years it has been losing market share to PSf). MCC is routinely used in pharmaceuticals and foods (see above). The reaction of the body to cellulose depends upon the type of cellulose, but generally is in the range of none to a light body reaction. The use of bacterial cellulose has been growing rapidly in recent years. Bacterial cellulose, obtained from *Acetobacter xylinium*, has shown surprising results as a wound dressing and a venture to commercialize its use has begun. Bacterial cellulose is also showing promise as a material for microsurgery.

Thus, while NCC has not yet been tested for biocompatibility, prior experience with cellulose in biomedical applications indicates that it will be biocompatible.

II. Dialysis Unit

A disclosed embodiment of a dialysis unit according to the present invention is based on a modified-microchannel architecture (MMA). This unit advances a new paradigm in haemotreatment. The design is a MECS-based, mass transfer/heat transfer/chemical reactor device for haemodialysis, haemofiltration and haemoreaction. This unit takes advantage of convective and diffusional motion of fluids (blood, dialysate, etc.), and dramatically improves (reduces the time, lessens the blood cell damage, etc.) device operation.

A. Technical Rationale

Figure 2A:
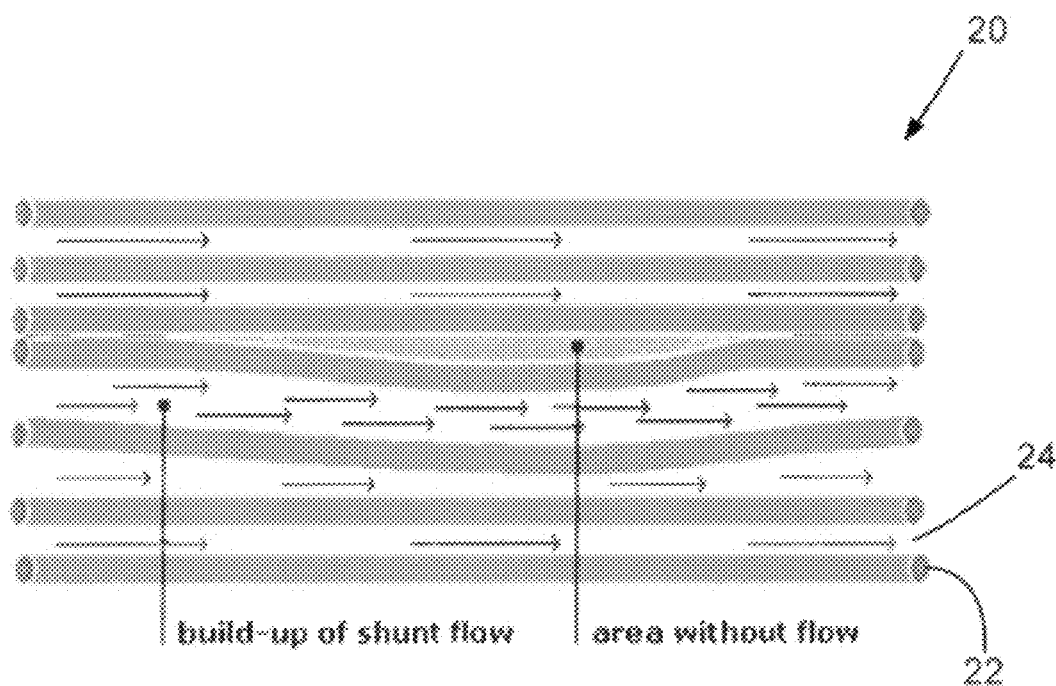
FIGS. 2A and 2B schematically illustrates flow mal-distributions that occur on a dialysate side of a conventional fiber-type dialyzer.
Figure 2B:
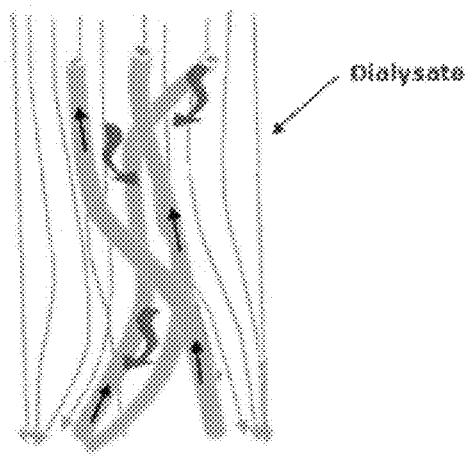

Mal-distribution of dialysate flow occurs due to uneven and inconsistent spacing between individual fibers in a conventional dialyzer. Areas with stagnant flow, as well as areas with developed shunt flow, dramatically reduce the efficiency of the mass transfer on the dialysate side. FIG. 2 schematically illustrates flow mal-distributions that occur on a dialysate side of a conventional fiber-type dialyzer 20. The spacing between individual fibers 22 is generally small, thus diffusion is an important mechanism of mass transfer in the inter-fiber space 24. The characteristic diffusion time from a membrane surface into the bulk of dialysate can be estimated as $\lambda_D = \lambda^2/D$ [s], where $\lambda$ [m] is the characteristic diffusion length (distance between the wall of the fiber and the center of the bulk flow) and D [m$^2$/s] is the diffusion coefficient of the diffusing molecule.

This characteristic diffusion time has to be compared with all other characteristic times ($\tau_d$—the mean residence time of dialysate, $\tau_b$—the mean residence time of blood flow through fibers, and $\tau_{HD}$—the overall duration of haemodialysis) pertinent to the operation of the conventional dialysis unit. An efficient dialyzer design requires that $\tau_D \ll \tau_d; \tau_b; \tau_{HD}$.

If the characteristic inter-fiber space 24 in regions with developed shunt flow is of the order of millimeters (10$^{-3}$ m) than the characteristic diffusion time $\tau_D$ is approximately 100 s. Previous research demonstrates that microscale devices radically reduce the characteristic time required for mass transfer in separation devices. Unlike the conventional dialysis unit, the microtechnology-based design of the disclosed embodiments maintain microscale dimensions evenly on both sides of the membrane. By maintaining the characteristic inter-fiber space substantially uniformly at 100 μm the characteristic time $\tau_D$ is about 1 s.

To optimize the dialysate flow distribution between the hollow fibers in a conventional dialyzer, one has to develop and implement additional 'static-mixer-like' implants that produce even and stable dialysate flow. This could potentially enhance the performance of the dialyzer. Developments in this direction are already evident in the design of the hollow fiber-type dialyzers among leading membrane manufacturers. However, MMA and microlamination technology allow for a much better and easier realization of an accurately engineered flow on both sides of the haemodialysis membrane. Moreover, the disclosed embodiments address major problems (blood cell damage, overall size of the device, haemotreatment duration, etc.) arising from current practices in haemodialysis and other haemotreatments.

B. Microscale Dialyzer Embodiment

Figure 3:
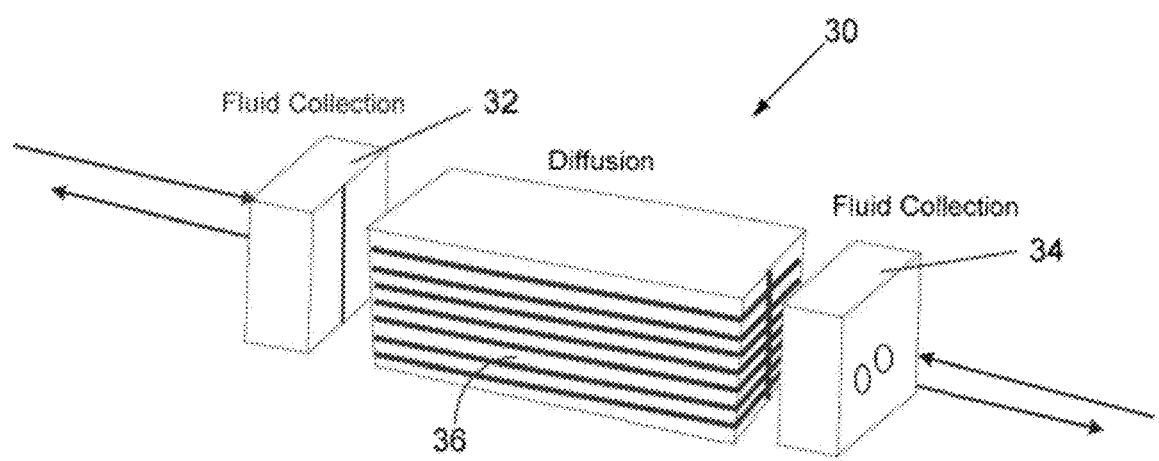
FIG. 3 illustrates one embodiment of a microscale dialyzer according to the present invention.
Figure 4A:
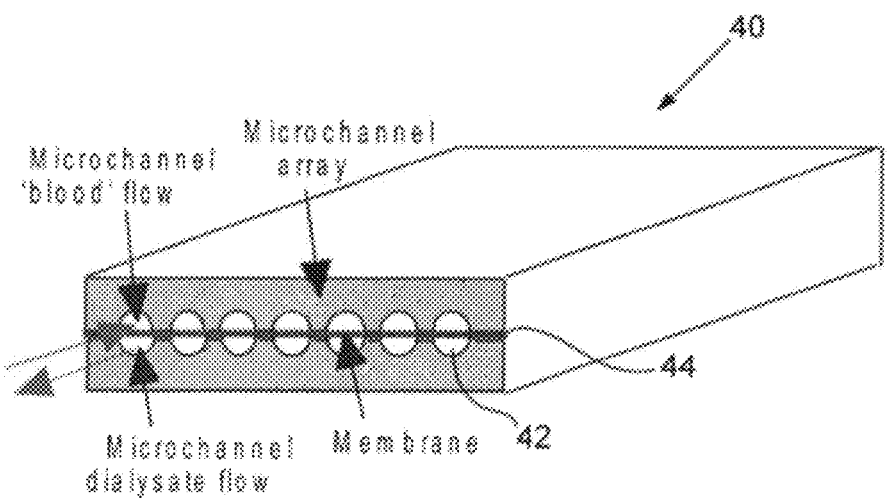
FIGS. 4A-4D are schematic diagrams illustrating one embodiment of a microchannel array having a filter membrane integrally associated therewith.
Figure 4B:
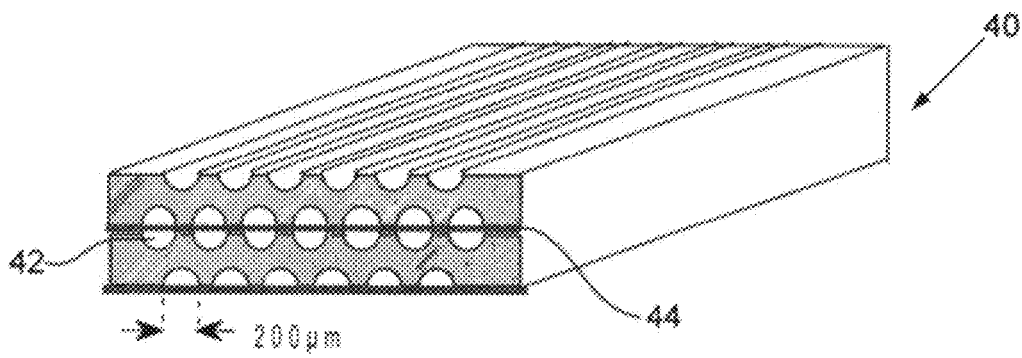
Figure 4C:
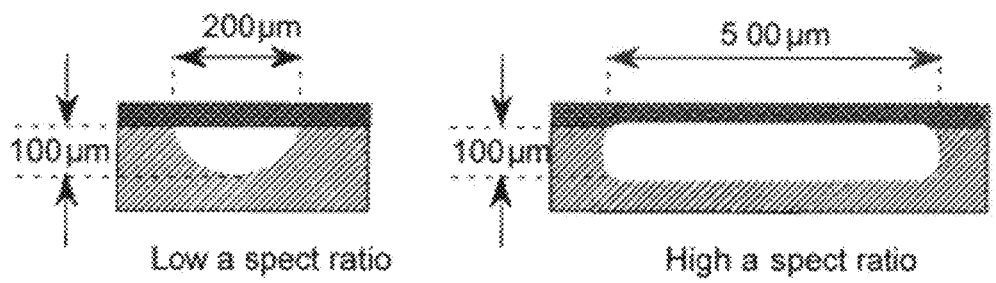
Figure 4D:
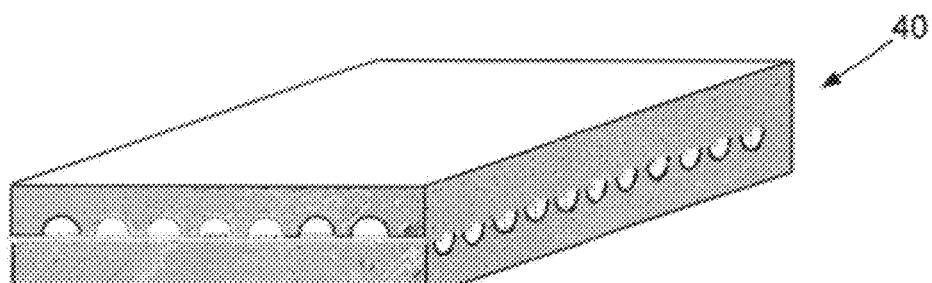

One embodiment of a microscale dialyzer 30 is illustrated in FIG. 3. FIG. 3 illustrates that the disclosed unit has fluid collection units 32 and 34 and at least one diffusion unit 36. The entire unit can be made using microlamination techniques. The diffusion unit 36 of the device can be made as a microchannel array. A schematic diagram illustrating a microchannel array 40 having a filter membrane integrally associated therewith is illustrated in FIG. 4. The illustrated embodiment 40 includes an array of microchannels 42 for blood flow and dialysate flow. These fluids are separated by a membrane 44, particularly a semi-permeable membrane, such as the NCC-polymeric composite membrane described above. A particular embodiment includes a nanocrystalline-cellulose/polysulfone membrane. The cross section of the microchannels 42 can be varied, as indicated in FIG. 4 to provide desired fluid flow characteristics and other beneficial properties.

Figure 5:
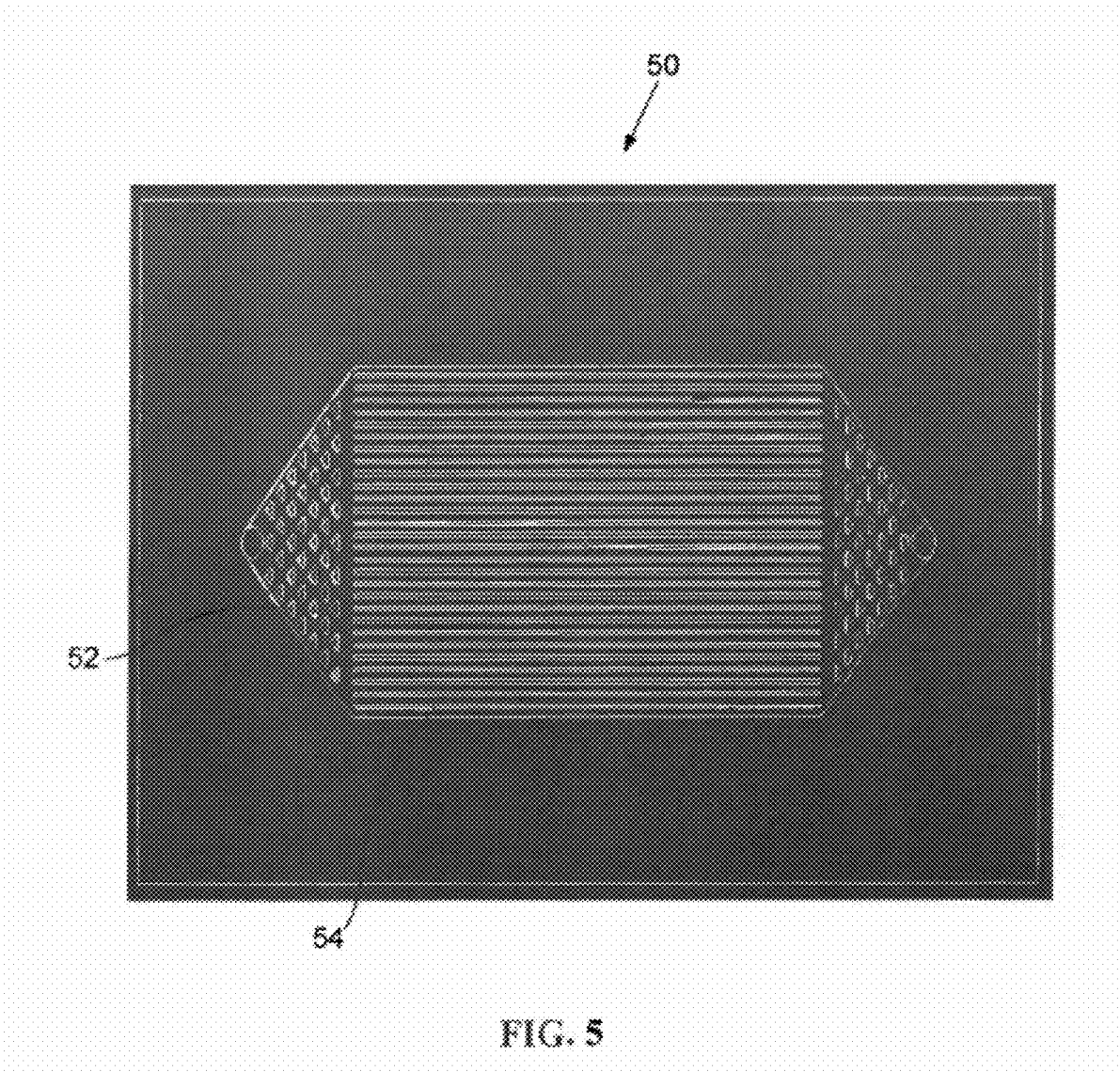
FIG. 5 is a plan view of one embodiment of a MECS dialyzer according to the present invention.

One embodiment of a MECS dialyzer design 50 is illustrated in FIG. 5. The size of the device is only 2-3 times the size of a dime (indicated by the coin placed adjacent the device in FIG. 6 of the priority provisional application incorporated herein be reference) for size comparison.

The combination of biocompatibility, stiffness and nanoscale filler dimensions afforded by cellulose nanocrystal-filled PSf allow the incorporation of microscale features (1-100 μm) in the MECS devices.

FIG. 5 illustrates the use of mixing posts 52 prior to the microchannels 54. The posts 52 provide a method for dispersing blood flow evenly throughout available microchannels 54 through which the blood will flow. These posts 52 can be physical portions of the device 50. For example, in the illustrated embodiment the posts 52 are triangularly shaped, and extend upwardly from a surface to impinge a fluid flowing over and about the posts. These posts 52 can have any geometric shape in addition to the triangular posts illustrated in cross section, including without limitation, cylindrical, rectangular, square, polygonal, and any combination of such shaped posts. The spacing and number of posts provided is determined by the desired end result, i.e. distribution of blood flow substantially equally among the available microchannels.

Other methods also can be used to disperse blood flow evenly within the microchannels. For example, the surface in contact with the fluid flow, such as blood flow, can be modified to have regions that are compatible with the flowing fluid and regions that are not compatible with the flowing fluid. Again by way of example, regions of the dialyzer surface can be made either hydrophobic or hydrophilic by surface modification. For dialysis, regions of the surface that are hydrophobic tend to repel the blood flow and thereby allow blood dispersion into the microchannels, much in the same manner as the mixing posts illustrated in the embodiment of FIG. 5.

Figure 6:
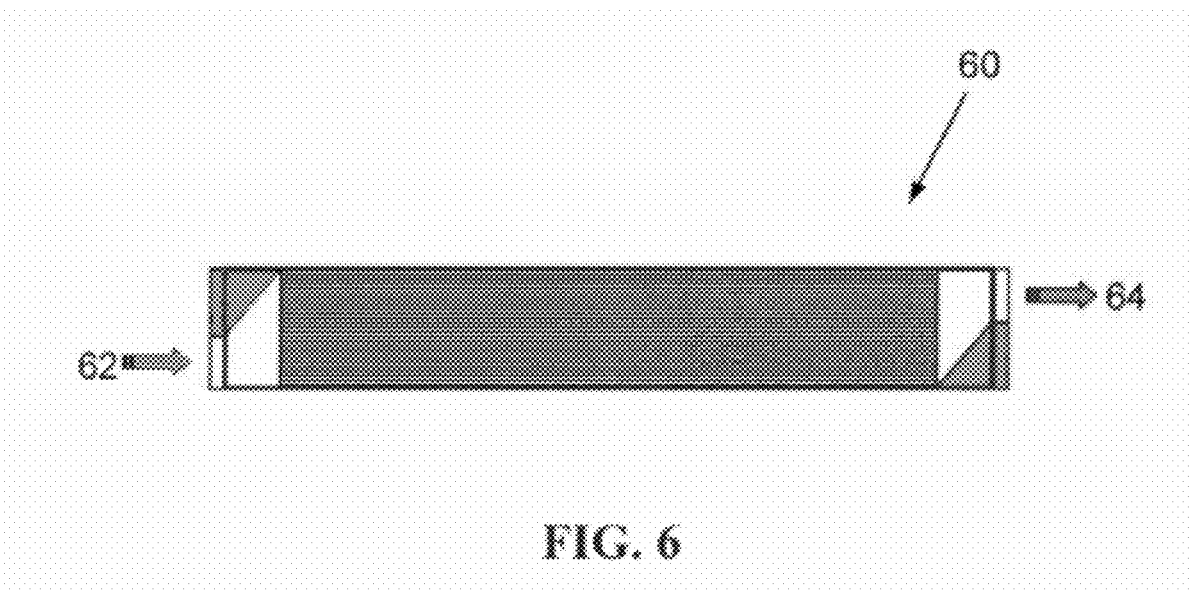
FIG. 6 is a plan view of the blood flow side and dialysate flow side of one embodiment of a dialyzer according to the present invention.

The microchannels in the illustrated embodiment have a blood flow side and a dialysate flow side. FIG. 6 is a plan view of a microchannel dialyzer 60, the blood flow side, side 62, and the dialysate flow side, side 64.

Illustrated embodiments of the present dialyzer unit typically are fabricated as a multilayered unit. These features are illustrated schematically in FIG. 7. The embodiment 70 depicted by FIG. 7 includes a top support plate 72 and a bottom support plate 74. Between the two support plates 72 and 74 are plural microchannel-defining plates. Three types of microchannel-defining plates are used to make the layered design illustrated in FIG. 7: a top, one-sided plate 76; plural middle, two-sided plates 78; and a bottom, one-sided plate 80. Positioned between the plural plates 76-80 are filter membranes 82, such as the nanocrystalline cellulose/polysulfone composite filter membrane described herein.

Diffusion channels can have a variety of configurations. Different diffusion units may have different microchannel configurations. Alternatively, a single diffusion unit of a disclosed dialyzer embodiment can have plural different microchannel configurations. Plural different channel configurations 82, 84 and 86 are schematically illustrated in device 83 of FIG. 8.

Figure 7:
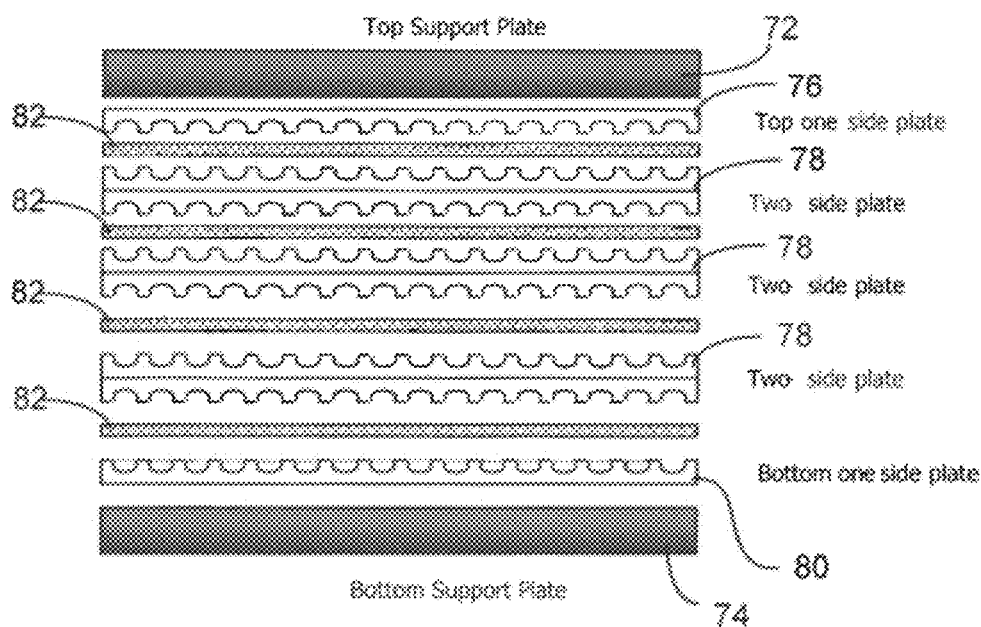
FIG. 7 is a schematic drawing illustrating a multi-layered dialyzer unit comprising multiple microchannel defining plates and integrally associated polymeric membranes.
Figure 8:
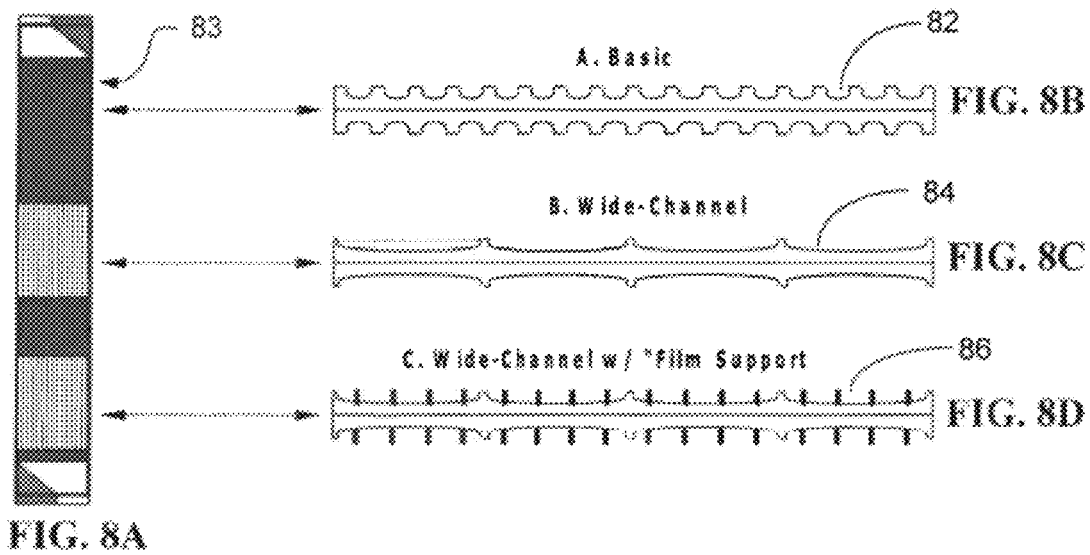
FIGS. 8A-8D illustrate plural different diffusion channel design configurations.
Figure 9:
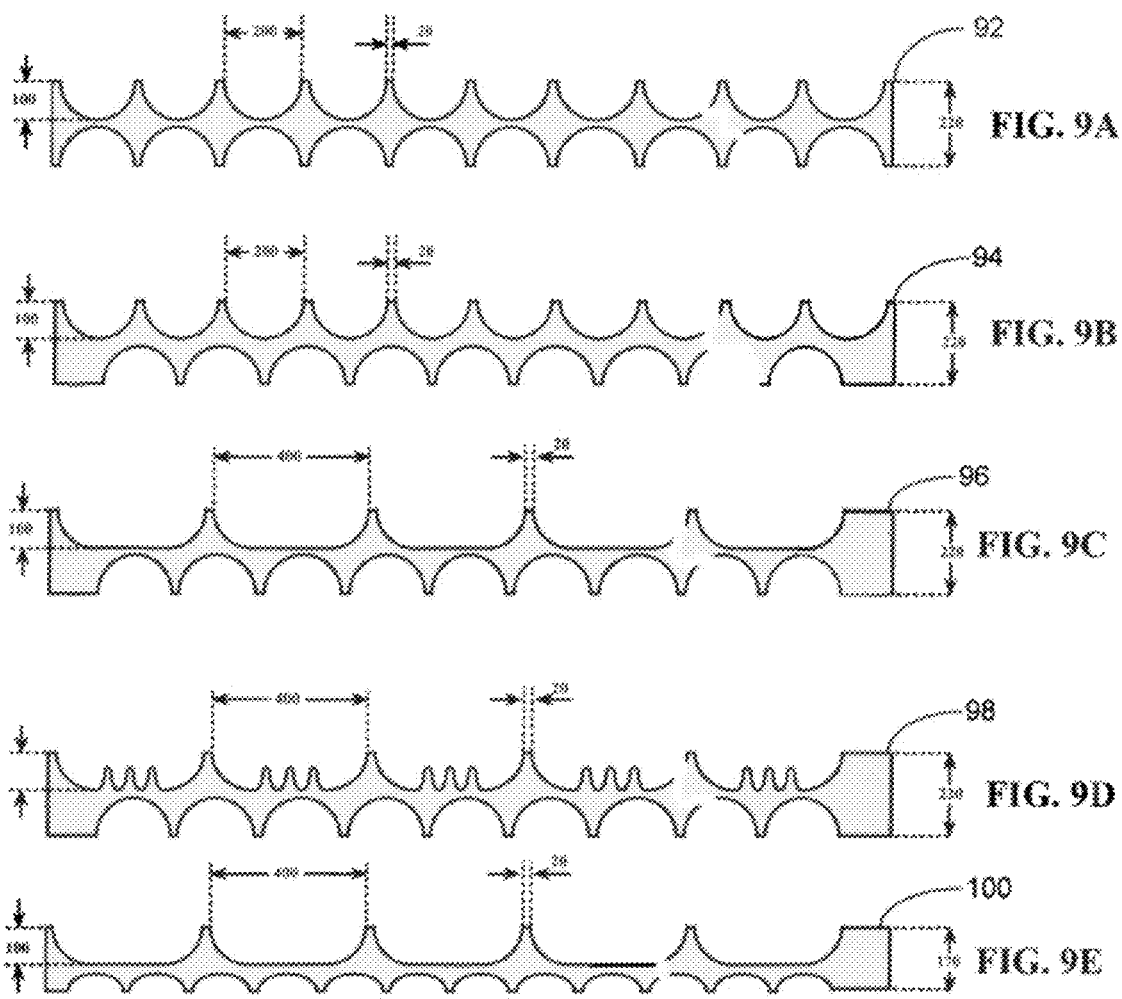
FIGS. 9A-9E provide typical dimensions used to make the plates illustrated in FIG. 8.

The dimensions of plural plates used to assemble a dialyzer unit also can vary to provide different functional results. Typical dimensions in microns used to make the plates illustrated in FIGS. 7 and 8 are provided by plates 92-100 of FIG. 9. A person of ordinary skill in the art will appreciate that these dimensions can be varied and still provide an operating dialyzer unit.

Figure 10:
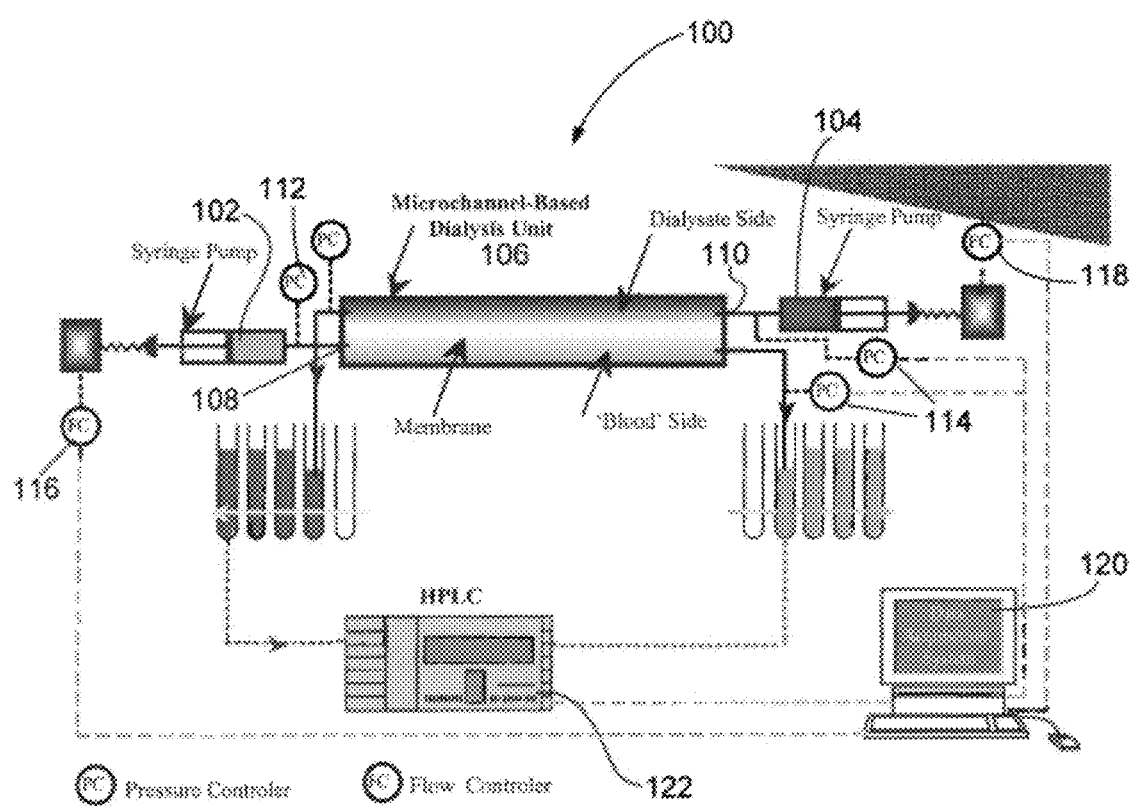
FIG. 10 is a schematic diagram illustrating one embodiment of an overall dialyzer system according to the present disclosure.

A schematic diagram illustrating one embodiment 100 of an overall dialyzer system is provided as FIG. 10. A device 102 for flowing blood to the microchannel-based dialysis unit, and a device 104 for flowing fluid to the dialysate side, are provided. In the illustrated embodiment, syringe pumps 102, 104 are fluidly coupled to the inlet sides 108, 110 of the microchannel-based dialysis unit 106. Optional pressure controllers 112, 114 can be placed in-line between one or more of the syringe pumps 102, 104 and the microchannel-based dialysis unit 106. Moreover, where necessary or desired, fluid flow controllers 116, 118 can be used to control fluid flow to one or more of the components of the system.

The microchannel-based dialysis unit 106 receives the fluids, which are separated into a blood flow side and a dialysate side. Different degrees of separation can occur in the disclosed unit. For example, a first separation may involve blood separation, whereby primarily blood cells are separated from the blood side leaving a remaining fluid having both biologically necessary components, such as proteins, as well as waste products, such as urea. This remaining fluid then can be subjected to additional dialysis to remove materials, such as urea, that are normally removed during dialysis. The blood cell stream and the remaining purified fluid stream then can be recombined for return to the patient.

As would be understood by a person of ordinary skill in the art, additional devices, such as analytical or computational devices, can be used in combination with the dialysis embodiment described herein. For example, one or more computers 120 can be used to acquire data, monitor system operation, fluid composition, etc. The embodiment 100 illustrated in FIG. 10 also includes an analytical separation device, such as a high pressure liquid chromatography device 122.

Figure 11:
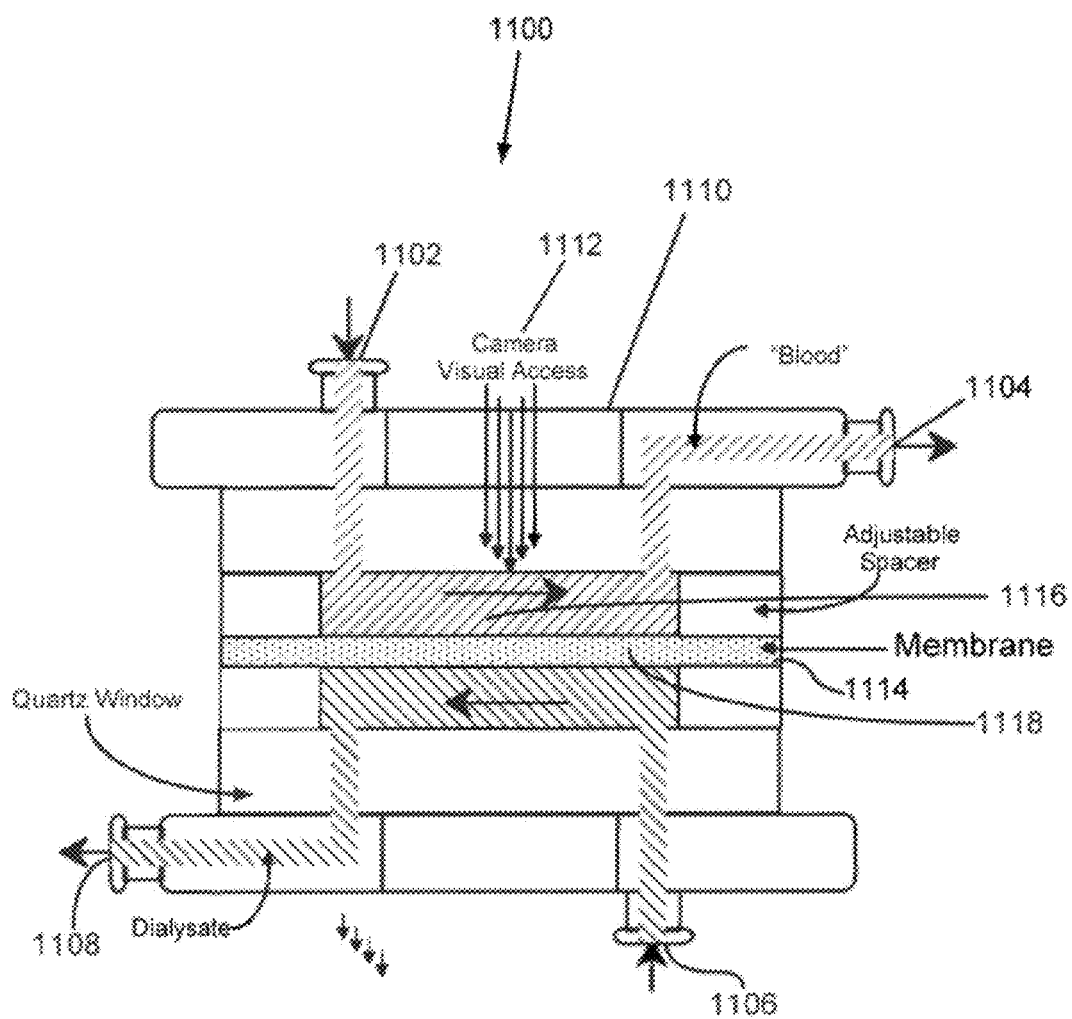
FIG. 11 is a schematic diagram of test device assembled to test microchannel-based fluid filtration.

A test device 1100 has been assembled to test microchannel-based fluid filtration. A cross sectional schematic view of such a test device 1100 is provided as FIG. 11. This test unit 1100 allows an operator to test different membranes for fluid separation. The test unit 1100 comprises a blood inlet 1102 and outlet 1104 and a dialysate inlet 1106 and outlet 1108. Fluid flow occurs through a quartz window 1110, which allows the operator and/or a camera 1112 to monitor fluid flow through the device 1100. Fluid flow is directed adjacent the two major planar surfaces 1116, 1118 of a separation membrane 1114, such as the nanocrystilline-cellulose/polysulfone composite membrane described herein.

Figure 12:
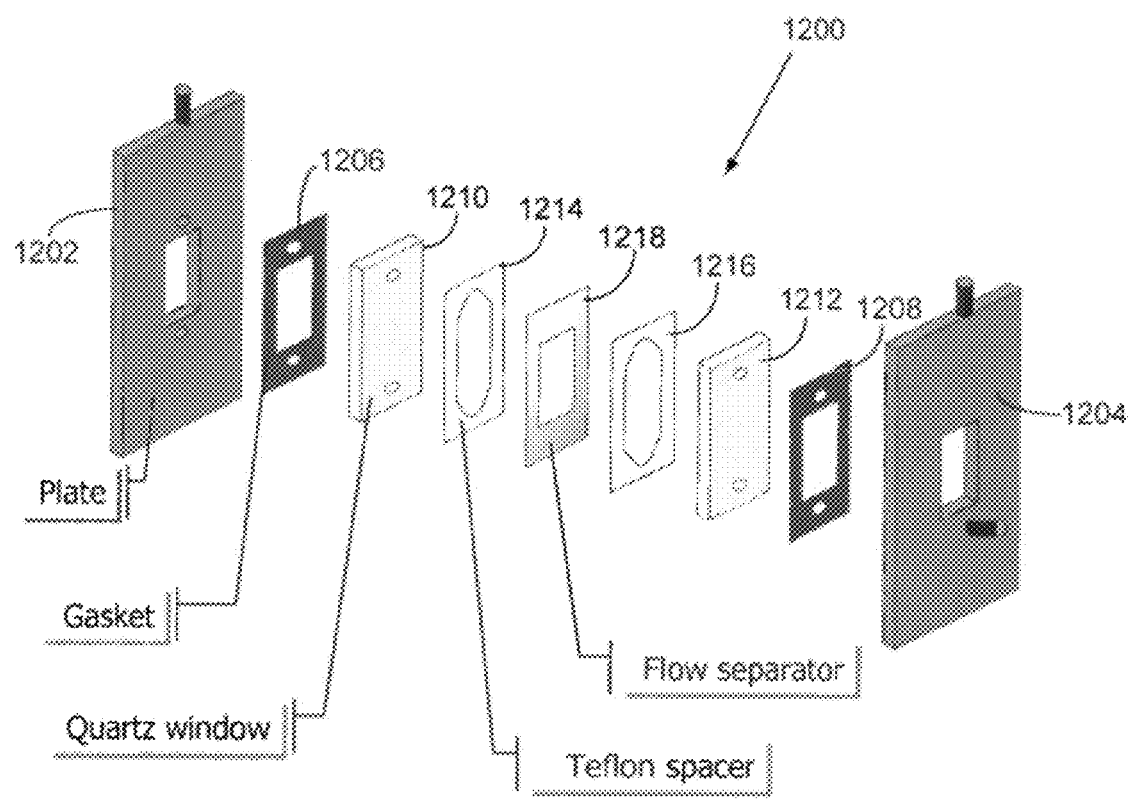
FIG. 12 is a schematic exploded view of a reactor developed to demonstrate operation of a dialyzer as disclosed herein.
Figure 14:
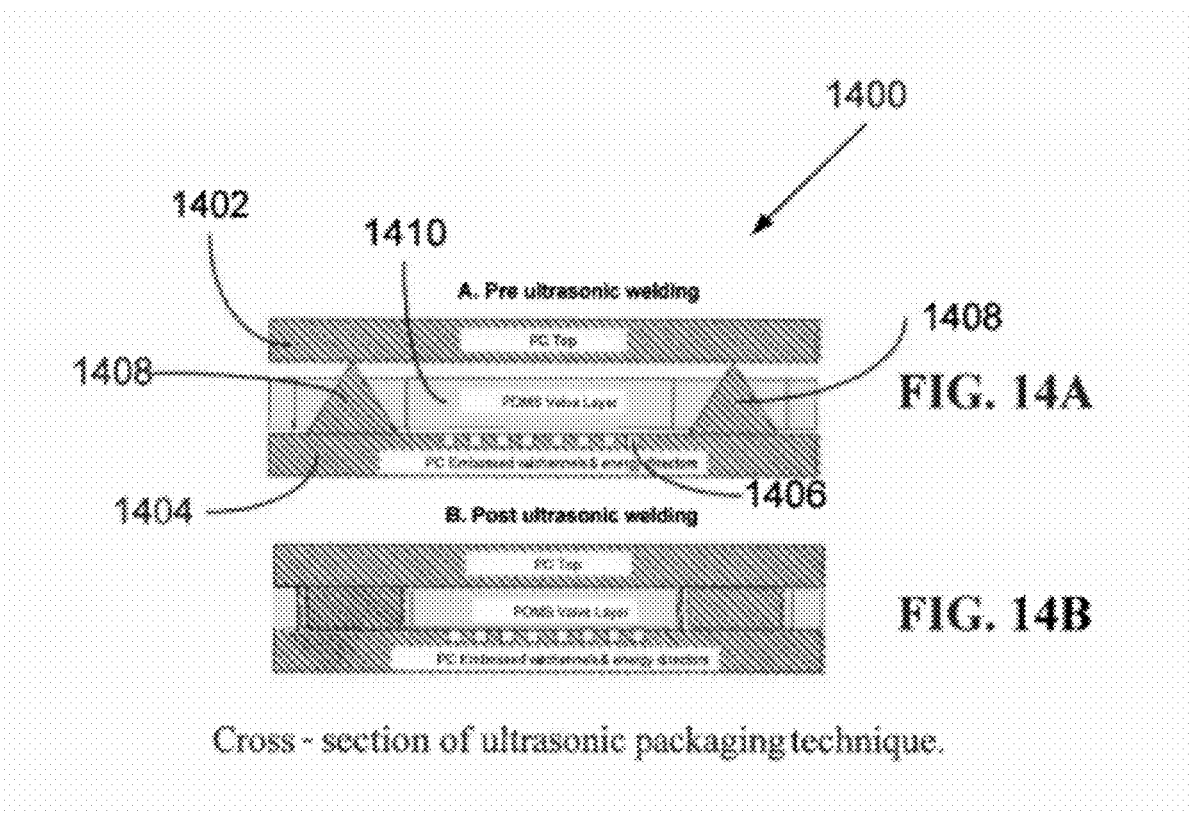
FIG. 14A is a schematic, cross sectional diagram illustrating an ultrasonic packaging technique before ultrasonically welding with the energy directors protruding above the PDMS layer.
FIG. 14B is a schematic, cross sectional diagram illustrating the result of ultrasonic welding with the energy directors melted down, bonding the top and bottom PC films, compressing the PDMS layer and sealing the microchannels.

A reactor has been developed to demonstrate operation of a dialyzer as disclosed herein. A schematic exploded view of one embodiment of a reactor 1200 is provided as FIG. 12. The reactor 1200 comprises a holder for the separation device, which comprises plural microchannel plates with a semipermeable membrane between them. The reactor allows interfacing the test separation device to other system components, such as pumps, tubing, reservoirs, etc. The illustrated reactor 1200 includes two end plates 1202, 1204. Gaskets 1206 and 1208 are positioned adjacent end plates 1202, 1204 for fluidly sealing the reactor 1200. Quartz windows 1210, 1212 are provided through which reactor operation can be monitored. Spacers, such as Teflon spacers 1214 and 1216, and a flow separator 1218 are provided to effectively space the reactor components. A photograph of a disassembled working embodiment of the reactor, adjacent a coin for size comparison, was provided as FIG. 14 in the priority provisional application.

Reactor 1200 is fluidly coupled to two fluid mixtures. These fluid mixtures are flowed through the reactor 1200 using a pump. Fluid flowing through the reactor 1200 flowed adjacent a membrane, thereby establishing that the combination of microfluidic channels and a membrane function usefully as a fluid separation/purification device.

III. Making Disclosed MECS Filtration Devices

A. Microlamination Method—General Discussion

Devices disclosed herein may be produced by a fabrication approach known as microlamination. Microlamination methods are described in several patents and pending applications commonly assigned to Oregon State University, including U.S. Pat. Nos. 6,793,831, 6,672,502, and U.S. patent applications Nos. 60/514,237, entitled High Volume Microlamination Production Of Mecs Devices, and 60/554,901, entitled Microchemical Microfactories, all of which are incorporated herein by reference.

Microlamination consists of patterning and bonding thin layers of material, called laminae, to generate a monolithic device with embedded features. Microlamination involves at least three levels of production technology: 1) lamina patterning, 2) laminae registration, and 3) laminae bonding. Thus, the method of the present invention for making devices comprises providing plural laminae, registering the laminae, and bonding the laminae. The method also may include dissociating components (i.e., substructures from structures) to make the device. Component dissociation can be performed prior to, subsequent to, or simultaneously with bonding the laminae.

In one aspect of the invention, laminae are formed from a variety of materials, particularly metals, alloys, including intermetallic metals and alloys, polymeric materials, including solely by way of example and without limitation, PDMS, polysulfones, polyimides, etc., ceramics, and combinations of such materials. The proper selection of a material for a particular application will be determined by other factors, such as the physical properties of the metal or metal alloy and cost. Examples of metals and alloys particularly useful for metal microlamination include stainless steel, carbon steel, phosphor bronze, copper, graphite, and aluminum.

Laminae useful for the microlamination method of the present invention can have a variety of sizes. Generally, the laminae have thicknesses of from about 1 mil to about 32 mils thick, preferably from about 2 mils to about 10 mils thick, and even more preferably from about 3 to about 4 mils thick (1 mil is 1 one-thousandth of an inch). Individual lamina within a stack also can have different thicknesses.

B. Laminae

1. Lamina Patterns

Lamina patterning may comprise machining or etching a pattern in the lamina. The pattern produced depends on the device being made. Without limitation, techniques for machining or etching include laser-beam, electron-beam, ion-beam, electrochemical, electrodischarge, chemical and mechanical material deposition or removal can be used. The lamina can be patterned by both lithographic and non-lithographic processes. Lithographic processes include micromolding and electroplating methods, such as LIGA, and other net-shape fabrication techniques. Some additional examples of lithographic techniques include chemical micromachining (i.e., wet etching), photochemical machining, through-mask electrochemical micromachining (EMM), plasma etching, as well as deposition techniques, such as chemical vaporization deposition, sputtering, evaporation, and electroplating. Non-lithographic techniques include electrodischarge machining (EDM), mechanical micromachining and laser micromachining (i.e., laser photoablation). Photochemical and electrochemical micromachining likely are preferred for mass-producing devices.

A currently preferred method for patterning lamina for prototyping devices is laser micromachining, such as laser numerically controlled micromachining. Laser micromachining has been accomplished with pulsed or continuous laser action in working embodiments. Machining systems based on Nd:YAG and excimer lasers are typically pulsed, while $CO_2$ laser systems are continuous. Nd:YAG systems typically were done with an Electro Scientific Industries model 4420. This micromachining system used two degrees of freedom by moving the focused laser flux across a part in a digitally controlled X-Y motion. The laser was pulsed in the range of from about 1 kHz to about 3 kHz. This provides a continuous cut if the writing speed allows pulses to overlap. The cutting action is either thermally or chemically ablative, depending on the material being machined and the wavelength used (either the fundamental at 1064 nm, the second harmonic at 532 nm, the third harmonic at 355 nm or the fourth harmonic at 266 nm). The drive mechanism for the Nd:YAG laser was a digitally controlled servo actuator that provides a resolution of approximately 2 µm. The width of the through cut, however, depends on the diameter of the focused beam.

Laminae also have been machined with $CO_2$ laser systems. Most of the commercial $CO_2$ lasers semi-ablate or liquefy the material being cut. A high-velocity gas jet often is used to help remove debris. As with the Nd:YAG systems, the laser (or workpiece) is translated in the X-Y directions to obtain a desired pattern in the material.

An Nd:YAG pulse laser has been used to cut through, for example, 90-µm-thick steel shims. The line widths for these cuts were approximately 35 µm wide, although with steel, some tapering was observed. For the 90-µm-thick sample, three passes were made using 1 kHz pulse rate, an average laser power of 740 mW, and a distance between pulses of 2 µm. Also, the cuts were made at 355 nm. Some debris and ridging was observed along the edge of the cut on the front side. This material was easily removed from the surface during lamina preparation, such as by surface polishing.

Laminae also have been patterned using a $CO_2$ laser. For example, a serpentine flexural spring used in a miniature Stirling cooler has been prepared using a $CO_2$ laser. The $CO_2$ through-cuts were approximately 200 µm wide and also exhibited a slight taper. The width of the $CO_2$ laser cut was the minimum achievable with the system used. The part was cleaned in a lamina preparation step using surface polishing to remove debris.

Pulsed Nd:YAG lasers also are capable of micromachining laminae made from polymeric materials, such as laminae made from polyimides. Pulsed Nd:YAG lasers are capable of micromachining these materials with high resolution and no recast debris. Ultraviolet wavelengths appear best for this type of work where chemical ablation apparently is the mechanism involved in removing material. Clean, sharp-edged holes in the 25-50 µm diameter range have been produced.

2. Lamina Preparation

In another aspect of the invention, lamina patterning includes lamina preparation. The laminae can be prepared by a variety of techniques. For example, surface polishing of a lamina following pattern formation may be beneficial. Moreover, acid etching can be used to remove any oxides from a metal or alloy lamina. In one embodiment of the invention, lamina preparation includes applying an oxide-free coating to some or all of the laminae. An example of this would be electroplating gold onto the lamina to prevent oxidation at ambient conditions.

In another embodiment of the invention, lamina preparation includes filling the spaces between the structures and substructures with a material, referred to herein for convenience as a fixative, that holds the structure and substructure together before bonding the laminae and after the fixture bridges are eliminated. For instance, investment casting wax can be used as the fixative to hold together the structure and substructure. The fixture bridges are then eliminated, and the substructure is maintained in contact with the structure by the fixative. The fixative is eliminated during or after bonding the laminae together, thus dissociating the substructure from the structure.

3. Laminae Registration

Laminae registration comprises (1) stacking the laminae so that each of the plural lamina in a stack used to make a device is in its proper location within the stack, and (2) placing adjacent laminae with respect to each other so that they are properly aligned as determined by the design of the device. It should be recognized that a variety of methods can be used to properly align laminae, including manually and visually aligning laminae.

The precision to which laminae can be positioned with respect to one another may determine whether a final device will function. The complexity may range from structures such as microchannel arrays, which are tolerant to a certain degree of misalignment, to more sophisticated devices requiring highly precise alignment. For example, a small scale device may need a rotating sub-component requiring miniature journal bearings axially positioned to within a few microns of each other. Several alignment methods can be used to achieve the desired precision. Registration can be accomplished, for example, using an alignment jig that accepts the stack of laminae and aligns each using some embedded feature, e.g., corners and edges, which work best if such features are common to all laminae. Another approach incorporates alignment features, such as holes, into each lamina at the same time other features are being machined. Alignment jigs are then used that incorporate pins that pass through the alignment holes. The edge alignment approach can register laminae to within 10 microns, assuming the laminae edges are accurate to this precision. With alignment pins and a highly accurate lamina machining technique, micron-level positioning is feasible.

Thermally assisted lamina registration also can be used as desired. Additional detail concerning thermally assisted lamina registration is provided by copending application No. 60/514,237, which is incorporated herein by reference.

Registration of laminae in a working embodiments typically was accomplished using an alignment jig or by thermal registration. If an alignment jig is used, it must tolerate the bonding step. Thus, in typical microlamination setups, the alignment jig preferably was incorporated into the design of the structure that compressed the stack for bonding. A person of ordinary skill in the art also will recognize that the registration process can be automated.

C. Laminae Bonding

Laminae bonding comprises bonding the plural laminae one to another to produce a monolithic device (also referred to as a laminate). Laminae bonding can be accomplished by a number of methods including, without limitation, diffusion soldering/bonding, thermal brazing, adhesive bonding, thermal adhesive bonding, curative adhesive bonding, electrostatic bonding, resistance welding, microprojection welding, and combinations thereof.

1. Microprojection Welding

Laminae can be bonded to one another at specific sites on the laminae by the novel process of microprojection welding. Microprojection welding comprises patterning lamina having at least one projection, and more typically plural projections, that extends from at least one surface, generally a major planar surface, of the lamina. Selective bonding is accomplished by placing laminae between electrodes and passing a current through the electrodes. The laminae are bonded together selectively at the site or sites of the projection(s). A person of ordinary skill in the art will recognize that a variety of materials suitable for welding can be used to produce the projections, including mild steel, carbon steel, low carbon steel, weldable stainless steel, gold, copper, and mixtures thereof. The welding material (i.e., projections) preferably is made of the same material as the laminae being bonded.

Microprojections suitable for microprojection welding can be produced by both additive and subtractive processes. In one embodiment of the invention, a subtractive process was used to pattern laminae. The subtractive process comprises etching away material from a lamina to produce the microprojections. A person of ordinary skill in the art will recognize that a variety of etching processes can be used, including photochemical and electrochemical etching.

In another embodiment of the invention, microprojections can be produced on laminae by an additive process. This additive process comprises building up a lamina to form the microprojections or building up the projections on a lamina prior to lamina patterning. One method of patterning the microprojections would involve either etching or depositing projections through a lithographic mask prior to lamina production. Lamina patterning should then be conducted with reference to the placement of these projections. For example, if the flapper valve pivot is too close to ring projections, then "flash material" may interfere with the operation of the flapper valve. "Flash material" is extraneous projection weld material or material produced by the welding operation.

Microprojections can have several geometries. For example, individual isolated protrusions can be used. Moreover, continuous lines, rings or any other geometries suitable for the welding requirements of a particular device, can be used to practice microprojection welding of laminae.

In one aspect of the invention, plate electrodes were used to deliver current sufficient to weld the laminae to one another. The laminae that are to be welded together are placed between and in contact with the plate electrodes. Optionally, pressure can be applied to place the laminae in contact with each other or the plate electrodes.

Typical projections of working embodiment had heights of from about 100 µm to about 200 µm, with diameters of about 125 µm or less. If the projections are shorter than 100 µm, electrical shorts may result. The weld nuggets produced by the welding operation had diameters of about 1.5-1.7 mm. It can be important to orient substructures on individual lamina so that weld nuggets patterned by the welding process do not overlap, and hence potentially interfere with the operation of, the substructures.

2. Diffusion Soldering

Diffusion soldering is a known method for filing joints. See, for example, D. M. Jacobson and G. Humpston, Diffusion Soldering, *Soldering & Surface Mount Technology*, No. 10, pp. 27-32 (1992), which is incorporated herein by reference. However, diffusion soldering has not been adapted for use in microlamination processes for bonding laminae one to another for MECS devices.

Diffusion soldering of laminae can be practiced using a number of material combinations, including both base metals and alloys and on surfaces that have been metalized. Two of the more versatile combinations are tin-silver and tin-indium. These two diffusion-soldering systems provide a low-temperature bonding process that results in intermetallic strong joints at the material interface.

Another attractive feature is that the bond produced by diffusion soldering can take considerably higher reheat temperatures than most conventional bonding methods. Because of these characteristics, diffusion soldering is well suited for producing microlaminated devices that must operate at moderate temperatures (i.e., up to approximately 500° C.).

The tin-silver system can work on any surface able to withstand moderate temperatures and capable of receiving a plating layer of the requisite metal. For many devices, steel and stainless steel offer a number of attractive characteristics for fatigue strength, magnetic properties, relatively low thermal conductivity (for stainless steel), and corrosion resistance.

The diffusion soldering method first comprises preparing and plating the surface of each lamina. A typical plating process comprises plating with a low temperature material and a high temperature material. These two materials typically form an intermetallic material by diffusion soldering.

More specifically, diffusion soldering may involve placing a first strike layer, such as a thin strike layer of nickel (approximately 0.5 μm) on a bare surface that will receive the nickel, such as a metal or alloy surface. This layer promotes adhesion of the other platable metals. Strike layers may not be necessary. Then, a second, generally thicker layer, such as a silver layer 1 μm-10 μm, more typically 2-5 μm thick, is plated over the first layer. Copper may be preferred as a bonding agent between the strike layer or the lamina and the high temperature soldering material because of its ability to readily bond to both nickel and silver. Copper can create a copper-silver intermetallic that is weaker than the surrounding material, and hence be the site of material failure in the device. Finally, a third low-temperature material layer, typically tin, is plated 1 μm-10 μm, preferably 2-5 μm thick over the second layer.

Working embodiments used a stack having alternating surfaces plated with either high-temperature or high-temperature and low-temperature material, such as silver or silver and tin. The two outside laminae typically have high-temperature material, such as silver, so that the final, bonded stack did not adhere to the alignment jig. If possible, non-bonded internal structures and cavities preferably have the silver layer on their surface. This is to prevent low-temperature material from flowing into features.

The bonding takes place by momentarily raising the stack temperature above the melting point of the low-temperature material (e.g., tin @ 232° C.) under a compression pressure sufficient to achieve the bond. At higher pressures, lower temperatures likely will be required to achieve adequate bonding. Working embodiments have used compression pressures of approximately 2 MPa to about 5 MPa. A compression pressure below about 2 MPa may not provide sufficient pressure to achieve adequate bonding. Air and other oxidizing atmospheres preferably are excluded at this point to avoid the creation of tin oxides and voids. However, with the surface properly prepared, the bonding process is rapid and complete. One important aspect is to maintain sufficiently low temperatures and pressures so that the lower temperature material does not flow into the features, causing restriction of flow therethrough or therein.

Bond strength and re-heat temperatures can benefit by heating the stack for a longer period of time at the bonding temperature, such as at least up to one hour. This allows tin to further diffuse into the silver and form stronger intermetallic compounds within the joint itself. Some evidence exists for ultimately forming a silver bond interspersed with intermetallic tin/silver particles yielding a high strength, moderate temperature joint. Indium can be used in place of tin to yield an even lower temperature (melting point of indium is 157° C.) bonding process.

3. Miscellaneous Bonding Methods

Polyimide sheet adhesives can be used to bond laminae together. Polyimide is a commercially available, high-strength, high-temperature polymer. For example, Dupont manufactures a polyimide sheet adhesive, Kapton KJ. Kapton KJ retains adhesive properties and can bond surfaces together when heated and compressed. Polyimide sheets form moderate strength bonds that also provide good sealing capability.

D. Component Dissociation by Eliminating Fixture Bridges

Component dissociation is accomplished by eliminating fixture bridges. It will be recognized that there are a variety of ways to eliminate fixture bridges, including vaporizing the fixture bridge by heating it to a sufficient temperature, chemically eliminating, such as by dissolving, the fixture bridge, and laser ablation of the fixture bridge. Combinations of these methods also can be used.

One method for vaporizing the fixture bridges comprises capacitive discharge dissociation. Capacitive discharge dissociation comprises applying a current through the fixture bridge sufficient to vaporize the fixture bridge. There are a variety of ways to apply current through a fixture bridge. Working embodiments of the method have placed a first electrode in contact with the structure and a second electrode in contact with the substructure to be dissociated. Current is passed between the electrodes.

In one embodiment of the invention, a DC power source was used to charge a capacitor. The capacitor was discharged to pass current through the electrodes. The temperature, the amount of current, and the power necessary to eliminate the fixture bridge often varies with the particular properties of the fixture bridge, including the material the fixture bridge is made of, its cross-sectional area, and its length.

In another embodiment of the invention, fixture bridges are eliminated by thermochemical dissociation. Thermochemical dissociation has the potential advantage of reducing debris that may form during fixture bridge elimination. Thermochemical dissociation comprises selectively heating the fixture bridges, in combination with chemical elimination. Selective heating of the bridge can be accomplished by applying current to the fixture bridge, heating with a laser and/or focusing a laser on the bridge. One way to apply current through the fixture bridge comprises placing electrodes at or near the ends of the fixture bridge and passing a current between the electrodes. In another embodiment of the invention, heating elements, or some other method for delivering thermal energy, can be used to selectively heat the fixture bridges.

Chemical elimination also comprises applying a sufficient amount of a chemical to eliminate the fixture bridges. The fixture bridges also optionally can be selectively heated to a temperature sufficient to help chemically eliminate them either prior to, subsequent to, or simultaneously with application of the chemical. There are a variety of chemicals that can be used to eliminate the fixture bridges, such as acids, particularly mineral acids, bases, oxidizing agents, and mixtures thereof. The concentration, pH, and temperature sufficient to selectively chemically eliminate the fixture bridges varies with the particular properties of the fixture bridge, including the material the fixture bridge is made of, the cross-sectional area, and the length. Preferably, an acid having a pH of less than about 3 and at a temperature above freezing temperature is applied to the lamina. Preferably, the fixture bridges are heated to temperatures from about 200° C. to about 300° C. If the laminae are made of a copper alloy, cupric chloride or ferric chloride can be used to chemically eliminate the bridge. If the laminae are made of steel, a mixture, such as a 1:1 volume mixture of HCl:$HNO_3$, can be used to eliminate the fixture bridge.

In another embodiment of the invention, fixture bridges are eliminated by laser ablation. In this embodiment, line-of-sight access to the fixture bridges from the exterior of the device is desired. The laser beam should be able to be focused onto the fixture bridge, which may require line-of-sight access. UV lasers are particularly useful as they ablate metals as well as polymers and ceramics with little heat affect and very sharply distinguished features. Laser ablation allows the fabrication of preassembled features in materials other than metals, such as polymer and ceramics. An Nd:YAG laser operating in the fourth harmonic (266 nm wavelength) would be an example of a UV laser with sufficient power to perform this operation.

Fixture bridges can be eliminated either prior to, subsequent to, or simultaneously with bonding of the plural laminae. In one embodiment of the invention, the fixture bridges are eliminated prior to the bonding of the plural laminae one to another.

The method of this invention can be used to fabricate freeform geometries and microfeatures within a device. Microfeatures are of the size of from about 1 μm to about 100 μm. The methods of the invention can be used to produce micro-scale and meso-scale devices. Micro-scale devices are of the size of from about 1 μm to about 1 mm, preferably from about 1 μm to about 500 μm, and even more preferably from about 1 μm to about 100 μm. Meso-scale devices are of the size of from about 1 mm to about 10 cm, preferably from about 1 mm to about 5 cm, and even more preferably from about 1 mm to about 1 cm. Arrays of preassembled, meso-scale devices can be fabricated with overall sizes of up to about 12.5 centimeters by about 12.5 centimeters.

IV. Bonding Heterogeneous Stacks of Polymers

A. Novel Methods for Bonding Heterogeneous Stacks of Polymers

Figure 13:
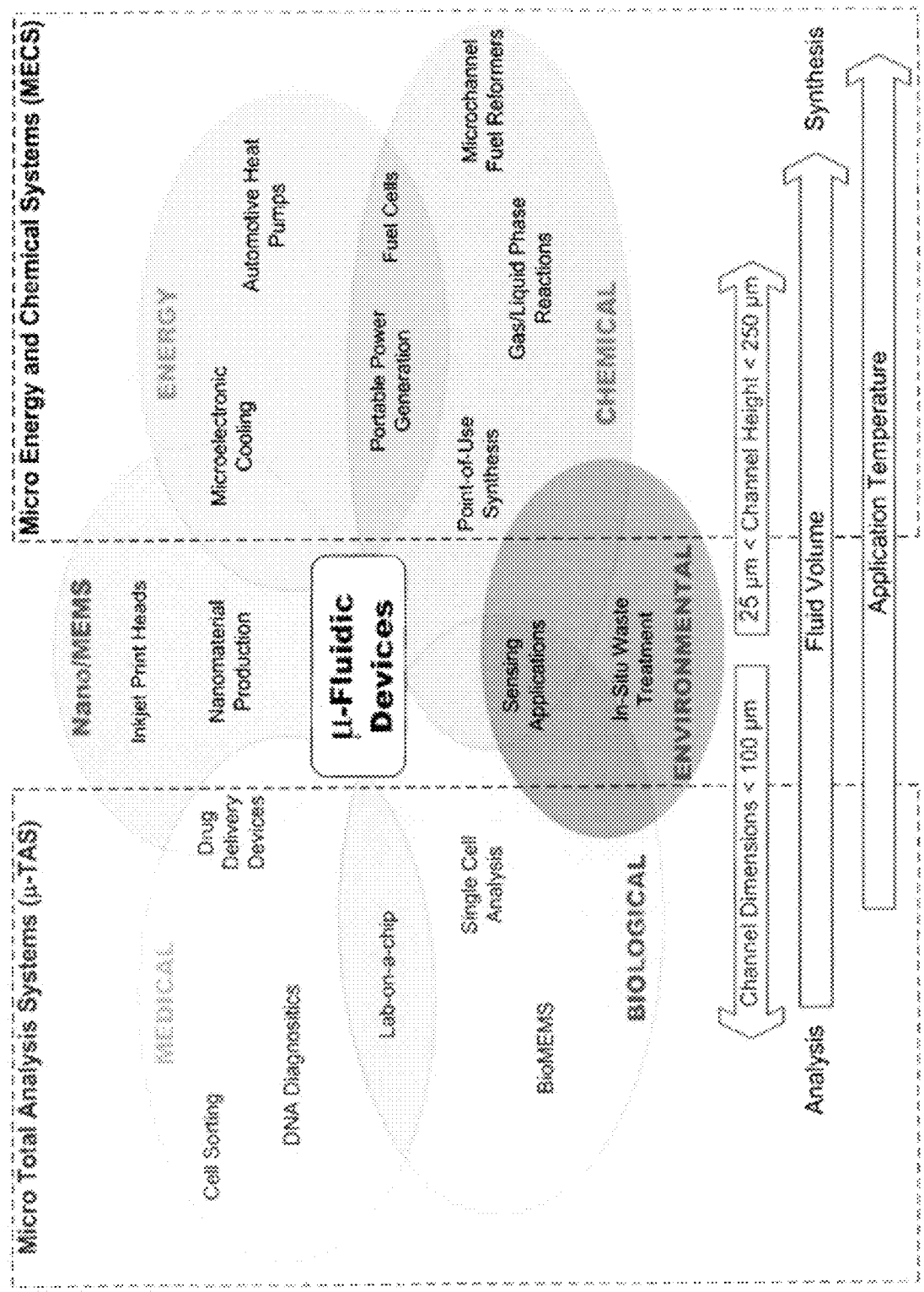
FIG. 13 illustrates different uses for MECS and micrototal analysis systems (µTAS).

Filtration units, such as a portable kidney dialysis unit, are bulk microfluidic devices because of the relatively larger volumes of fluid that are processed in microchannels over traditional "lab-on-a-chip" technology. Microchannel cross-sections can be produced to handle these fluid flows using highly-parallel arrays of microchannels. FIG. 13 provides an indication of the different uses for MECS and micrototal analysis systems (μTAS).

B. Requirements for Membrane Integration

MECS devices may integrate various types of membranes within a microlaminated stack. Examples include, without limitation: integrating Pd membranes for hydrogen separation within microchannel fuel processing systems; integrating contactor membranes in microchannel absorbers for use in heat pumps; integrating separation membranes into microchannel dialyzers for portable kidney dialysis; integrating elastomeric membranes into highly-branched networks of microreactors for molecular manufacturing (e.g. dendrimer synthesis); liquid-gas contactor useful for absorption of a gas, such as oxygen into a liquid, such as blood; separating $CO_2$ and/or $H_2S$ from natural gas; water purification such as by separating organic materials, such as organic acids from water. In each of these examples, heterogeneous materials must be integrated into a laminated stack.

A number of factors typically are considered to integrate membranes within embedded microchannel systems. For example, membrane materials generally are quite expensive, and therefore it is desirable to minimize the amount of membrane material used. This can be accomplished using a second, less expensive packaging material that needs to be integrated with the membrane material.

Also, membrane materials may have specific nano- or micro-morphologies which dictate the mass transfer of the membrane. These morphologies often are sensitive to heat, pressure and other processing conditions. Therefore, these materials cannot be conveniently patterned into geometries compatible with microchannel designs. A mechanism therefore is needed to incorporate the raw material form within the microlaminated stack.

Many techniques used to bond together elements made from a single material are less suitable for bonding together elements made from different materials. An example might be ultrasonic welding or thermal bonding of two polymers with significantly different glass transition temperatures where the structural form of one is compromised at a temperature lower than would be used for welding the second polymer. Also, solvent welding is complicated because different solvents are needed for different materials. Finally, plasma oxidation produces excellent welds between polydimethylsiloxane, polyethylene or polystyrene, but cannot be used effectively for other combinations of materials.

Membranes often have a thickness, or are made out of a material, that results in poor stiffness. Consequently, one non-trivial factor is producing a microchannel array with interspersing membranes that do not result in significant fin warpage and channel non-uniformities. Channel non-uniformities can lead to flow maldistribution, which negatively impacts the effectiveness of heat exchangers and microreactors.

The low modulus of some membranes requires that the layers be thick (on the order of one mm) in order to maintain dimensions. Therefore, in order to reduce the fluid volume of the MECS device being developed while meeting its processing and operating requirements, it is desirable to integrate the elastomeric capabilities of certain materials, such as PDMS, with a stiff material.

While some membranes are excellent candidates as valve membranes or other purposes, they are not good for packaging. One issue with separation membranes is that they are highly gas permeable, which can cause evaporation in microchannels leading to vapor-lock.

Another issue is that most membranes are not suitable as substrates for thin film deposition of heaters and thermocouples. Therefore, where such devices are required, new methods must be developed for their incorporation into working devices.

C. Membrane Integration Techniques—PDMS Integration

One method for bonding PDMS to another surface involves plasma oxidation of the PDMS surface, followed by conformality to the faying surface. Plasma oxidation introduces silanol (Si—OH) groups on the surface of PDMS. The condensation reaction of these groups with other appropriate functional groups [such as —OH, —COOH, carbonyls (—C=0), etc.] on the surface of another material or PDMS forms a strong bond between the two surfaces and immobilizes the grafted layer. This approach has several problems. First, the oxidized PDMS surface becomes inactive if not stabilized in aqueous solution within minutes after plasma oxidation. Second, it is compatible with only a handful of materials including glass, silicon, silicon oxide, silicon nitride, polyethylene and polystyrene. Silicon and glass surfaces are expensive relative to polymeric surfaces for long-term development. The only two polymers, polystyrene and polyethylene, which can be grafted to PDMS are not suitable for thin film deposition. Ticona Topas (COC), Zeonor 1600 and GE HPS1/HPS2 are examples of structural polymers having excellent optical clarity, high modulus, high glass transition temperature (>150° C.) and low gas permeability suitable for thin film deposition. Therefore, integration of PDMS with cheap, structural polymers would be highly desirable.

One specific approach for integrated PDMS membranes is to formulate copolymers with protected functionality under atmospheric conditions, which will polymerize under selective exposure to UV light. A first procedure concerns hydride functional (Si—H) siloxanes that have been incorporated into silanol elastomer formulations to produce foamed structures. Based on this, a novel and plausible approach to impart bonding character on PDMS, without plasma oxidation, is to incorporate a small amount (less than 1%) of silanol functional siloxane (or polysilsesquioxane) into the vinyl-addition siloxane formulation and selectively cure the blend. Also, a methacrylate or acrylate functional siloxane copolymer (which cures on exposure to UV) can be incorporated into the vinyl-addition siloxane such that selective curing of the blend can be used to bond surfaces. Oxygen inhibits the polymerization of methacrylate, but the methacrylate functionality can be protected in the presence of oxygen and unprotected to obtain a reasonable cure when blanketed with nitrogen or argon during UV exposure.

D. Physical Constraint

Another approach to membrane integration is to physically constrain membrane layers between stiff layers of molded polymers (e.g. Ticona Topas COC, Zeonor 1600 and GE HPS1/HPS2). Because of the stiffness of these materials, each makes an excellent candidate for ultrasonic welding. In addition, as thermoplastics, each has the ability to be thermally bonded (PDMS has a degradation temperature well above the Tg of these materials) and solvent welded.

Ultrasonic welding has enabled integration of the microinjection, microreaction, microseparation, detection and microextraction subsystems within a microreactor design for synthesizing dendrimer molecules. One goal of this architecture has been to minimize dead space within the microsystem by using stiff polymer films in place of thick PDMS substrates used in previous work for homogeneous PDMS microsystem integration. However, these same concepts of physical constraint can be extended to many different heterogenous microlaminated platforms.

E. Ultrasonic Welding

A current method involves sandwiching a PDMS valve membrane between two polycarbonate layers using ultrasonic welding. In order to accomplish this, angled channels are machined into a stainless steel substrate after Ni electroforming and resist stripping. These produce raised ridges during embossing that act as energy directors for ultrasonic welding.

The elastomer valve membrane layer can be produced by spin casting a suitable polymeric material or polymeric precursor, such as a PDMS monomer, onto a wafer with raised photoresist features that produce the valve chambers. The polymer is then cured. Openings for protrusion of the ultrasonic energy directors are then laser machined. It will be understood that this PDMS membrane layer could be replaced by any off-the-shelf membrane. FIG. 14A is a schematic, cross-sectional diagram of a microchannel array 1400 having a polycarbonate top plate 1402, and a polycarbonate bottom plate 1404 with enclosed microchannels 1406. Energy directors 1408 are provided either as separate units, or as defined by plate 1404. Array 1400 also includes a valve layer, such as a polydimethylsiloxane layer 1410.

Figure 15:
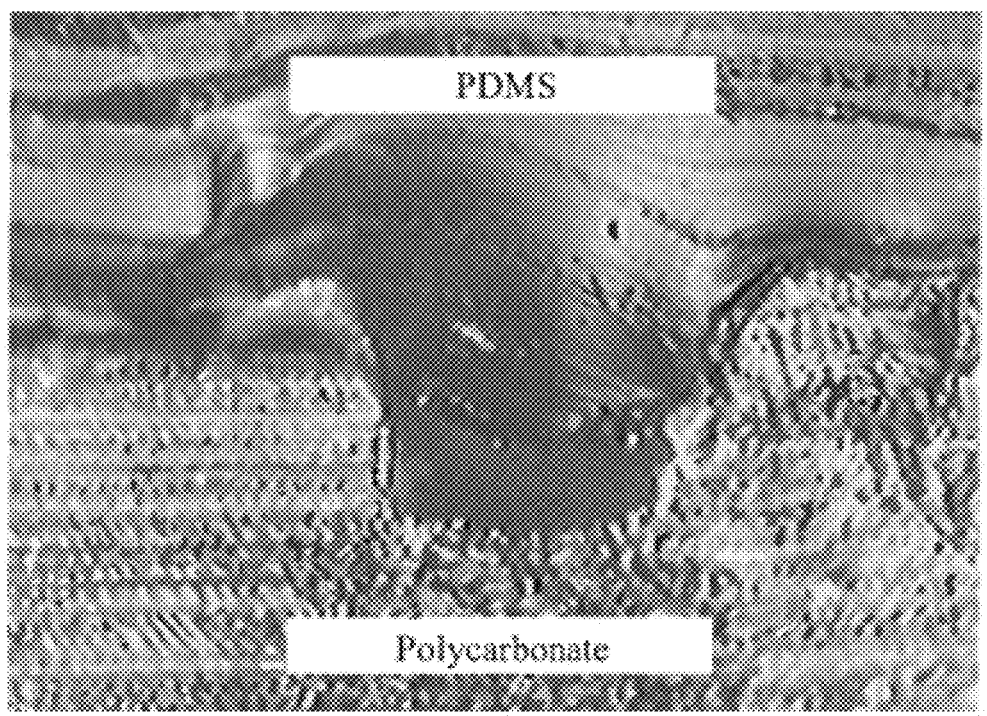
FIG. 15 is a photomicrograph illustrating that with appropriate welding time and pressure the energy directors form strong bonds and the PDMS compresses to create a conformal seal against the polycarbonate top and bottom.

FIG. 14A illustrates the array 1400 prior to ultrasonically welding with the energy directors 1408 protruding above the PDMS layer 1410. FIG. 14B diagrams the result of ultrasonic welding the array 1400 with the energy directors 1408 melted down, bonding the top and bottom PC films 1402 and 1404, compressing the PDMS layer 1410 and sealing the microchannels 1406. With appropriate welding time and pressure the energy directors form strong bonds and the PDMS compresses to create a conformal seal against the polycarbonate top and bottom as shown by FIG. 15.

F. Packaging Heterogeneous Stack of Polymeric Materials

Methods are needed to encapsulate a heterogeneous stack of materials, such as heterogeneous stacks of lamina made from various polymeric materials. Two alternative embodiments are disclosed for enclosing the heterogeneous stack of laminae. First, with the use of ultrasonic welding, thermal bonding and solvent welding to physically constrain the membrane across the membrane, the bonding technique can completely encapsulate the membrane after bonding with the packaging material. Second, if the bonding process is unable to fully encapsulate the membrane materials, a dip, spray, injection, cast or other application of a packaging material can be used to ultimately encapsulate the device. Care is taken with regard to fluidic, electrical or other types of interconnect.

G. Membrane Tension

Flow maldistribution in microchannels can be a significant problem associated with microfluidic devices. Certain embodiments of the present invention include a membrane between two adjacent laminae. The membrane preferably does not deflect substantially into the microchannel and hence create either channel blockage or flow maldistributions within the channel. Thus, processes have been devised to maintain the membrane slightly under tension, such as by stretching it, and thereafter affixing it in place relative to adjacent laminae.

A first method for maintaining a membrane under slight tension during processing is to mechanically constrain the membrane under tension. For example, a membrane may be patterned to include throughcuts for receiving protrusions on a first lamina. The distance between the two protrusions is slightly greater than the distance between throughcuts in the membrane. Registering the membrane with the adjacent lamina(e) so that the protrusions are inserted into the membrane throughcuts places the membrane in tension prior to or simultaneously with fixing in place the laminae and membrane, such as by welding the architecture, to form the final device.

There are alternative methods for maintaining the membrane in tension. For example, a first positive feature might be patterned into a first lamina to be positioned adjacent the membrane. The positive feature is sized and shaped to be received in a receiving slot, i.e., a negative feature, in a second lamina positioned adjacent the membrane. The positive and negative features on the adjacent non-membrane laminae preferably provide substantially equal force to the membrane as they mate. This can be achieved, for example, by using an O-ring or parallel-line type configuration. A positive circular or line feature is patterned in a first lamina and a negative, mating circular pattern or channel is machined in a second lamina. By coupling together the first lamina and second lamina so that the positive and negative features mate, the membrane is both (1) placed under sufficient tension to minimize or substantially eliminate membrane deflections into the microchannel, and (2) fixed in position relative to the adjacent laminae. The tension applied is just that amount of tension that facilitates minimizing or preventing membrane deflection into adjacent microchannel. This tension may vary, but likely ranges from a minimum tension force that is just greater than the material tension in a layer without application of a tension force to a maximum force that is below that which would result in material failure.

In a commercial production process, the membrane may be provided reel-to-reel, and hence the membrane material likely is in limited tension. Thereafter the membrane is positioned relative to adjacent laminae in a continuous or semi-continuous process. Alternatively, the membrane may be provided as a sheet. Whatever the method of deploying the membrane, it is likely that plural membranes for plural devices will be defined by a single sheet of polymer. Adjacently positioned packaging laminae also likely will define plural different components. The stacks may be de-paneled, whereby excess material in a membrane layer or packaging laminae is removed, and/or an original number of individual parts as defined by a single sheet, portion of a sheet and/or laminae, is reduced to a smaller number by cutting. Eventually, the device must be singulated from the remaining parts, which also can be done by laser cutting.

A second method for maintaining a membrane under tension comprises placing the membrane in a frame designed to place the membrane under tension. The frame construction can be patterned after the O-ring or parallel line type constructions exemplified above with respect to adjacent laminae. By mating the first and second frame parts, the membrane material placed between them is placed under tension. The stretched membrane is then positioned relative to other laminae to define the final architecture of the desired device. The membrane material then may be fixed in placed prior to joining laminae, such as by laser spot welding or solvent spot welding, followed by joining laminae together, such as by welding, to form the final device. It also may be possible to weld the entire device, such as by microwave welding, so that all laminae are fixed in their positions simultaneously. Microwave welding is described in copending provisional application No. 60/715,466, which is incorporated herein by reference.

V. Incorporating other Devices into an Operational System

Embodiments of the present invention have been disclosed with reference to filtration and purification methods, and devices therefore, with one particular embodiment comprising a dialysis unit. This unit can be coupled with other operating devices to provide a system useful for a variety of applications. For example, the system can include a microchemical microfactory for manufacturing useful biological molecules. The system also can include, again solely by way of example, micromixers for mixing fluids that need to be combined, or recombined, such as with the blood cell and ultrafiltered fluid streams that result from using the dialysis unit embodiments disclosed herein.

A. Material Synthesis

Figure 16:
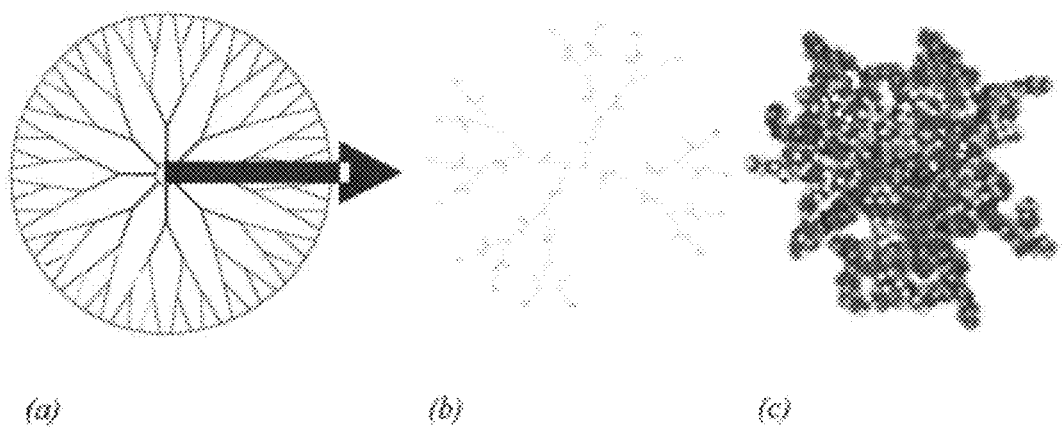
FIG. 16 is a diagram of (a) a "nanofractory" producing the generalized structure of a dendrimer as (b) a branched architecture and (c) a 3-D space-filling model.

Microreactor-based dendrimer production within fractal nanofactories (or "nanofractories") is disclosed herein, which allows the ability to control hundreds of parallel reactions necessary to economically produce dendrimers for societal impact. Dendrimers are highly-branched, nanometer-sized molecules with fascinatingly symmetrical fractal morphologies. See FIG. 16. The word dendrimer (coined by Tomalia et al.) is derived from the Greek words dendri (branch, tree-like) and meros (part of). Dendrimers consist of a core-unit, branching units, and end groups located on their peripheries. Their dendritic architecture presents great potential for a wide variety of applications. Dendrimers hold great promise as building blocks for complex supramolecular structures and as nanoscale carrier molecules in drug delivery, where nanoparticles and nanocapsules are gaining popularity. The molecules can be assembled with startling precision, a necessity when the goal is construction of nanoscale structures or devices with sophisticated and complex functionality. Along with targeting tumor cells and drug delivery systems, dendrimers have shown promising results as tools for MRI imaging and gene transfer techniques. Also, dendrimer-based nanocomposites are being studied as possible antimicrobial agents to fight *Staphylococcus aureus, Pseudomonas aeruginosa*, and *Escherichia coli*. The structural variety of dendrimers, yielding molecules having differing optical, electrical, and chemical properties, makes them potentially even more attractive in these applications.

Dendrimers have been shown to act as scavengers of metal ions, offering the potential for use in fluid purification, such as water purification, and environmental clean-up applications. Their size allows them to be filtered out post-extraction using common ultrafiltration techniques.

A critical barrier to the routine use of dendrimers is the tedious, expensive means of their synthesis. This synthesis consists of two constantly repeating reaction steps involving: 1) coupling a central unit to two branching units; and 2) activating the branches so they can react further. Two general approaches (divergent and convergent) to dendrimer synthesis exist. Divergent synthesis starts from a seed and progresses towards the periphery of the dendrimer, while convergent synthesis proceeds from the periphery to a core.

B. Divergent Synthesis

The divergent approach, arising from the seminal work of Tomalia and Newkome, initiates growth at the core of the dendrimer and continues outward by the repetition of coupling and activation steps. In divergent synthesis, several hundred steps may be required to obtain five or six dendrimer generations (sizes of interest). In this case the yield for each step multiplies through to determine the total yield. For example, in the synthesis of a fifth generation poly (propylene imine) dendrimer (64 imine groups; 248 reactions), a yield of 99% per reaction will result in only $0.99^{248}=8.27\%$ of defect-free dendrimer. The similar sizes of defective and defect-free dendrimers then make separation difficult further complicating matters. Exponential growth in the number of reactions to be performed to produce higher generations makes divergent synthesis an unlikely method for the production of uniform dendrimers beyond generation five or six unless the yield at each step exceeds 99.8%. In addition, extremely excessive amounts of reagents are required in latter stages of growth to reduce side reactions and force reactions to completion. This not only increases the cost but also causes difficulties in purification.

C. Convergent Synthesis

Convergent synthesis, first reported by Hawker and Fréchet in 1989, initiates growth from the exterior of the molecule, and progresses inward by coupling end groups to each branch of the monomer. The single functional group at the focal point of the wedge-shaped dendritic fragment can be activated after the coupling step. Coupling the activated dendrons to a monomer creates a higher generation dendron. Finally, the globular multi-dendron dendrimer is generated by attaching the dendrons to a polyfunctional core. Here, a small and constant number of reaction sites are maintained in each reaction step. Consequently, only a small number of side products are possible in each step. As a result, the reactions can be driven to completion with only a slight excess of reagent and defective product can be eliminated prior to subsequent reaction. Thus, convergent synthesis has the potential to produce purer dendrons and dendrimers than divergent synthesis. Furthermore, the ability to precisely place functional groups throughout the structure, to selectively modify the focal point, and to prepare well-defined asymmetric dendrimers make the convergent approach attractive. However, since the coupling reaction occurs only at the single focal point of the growing dendron, the preparation of higher generation dendrons and dendrimers (typically above the sixth generation) is sterically hindered, resulting in decreased yields. This is especially evident in the reaction between high generation dendrons and the core. This drawback has limited the commercialization of dendrimers produced by convergent synthesis. Our nanofactory approach to convergent synthesis will address this drawback.

D. Synthesis using Microsystems

Chemical synthesis, such as dendrimer synthesis (and nanoproduction in general), can be facilitated through the improved process control made available by highly-paralleled, process-intensified microsystems. Microreaction technology transforms current batch nanoproduction practices into a continuous process with rapid, uniform mixing and precise temperature control. Dendritic macromolecules can be manipulated using micro- and nanofluidic mixers. Microseparations and microextraction technology minimize reagent requirements and defective product to further improve yields in downstream reactions. In addition, microsystems provide the advantage of eliminating air contact, thereby minimizing contamination and improving yield. Furthermore, microsystems technology minimize environmental impact of nanoproduction using solvent free mixing, integrated separation techniques and reagent recycling. Finally, the possibility of synthesizing nanomaterials in the required volumes at the point of use, eliminates the need to store and transport potentially hazardous materials.

Dendrimer production can be implemented within a fractal nanofactory, or "nanofractory". The nanofractory spatially intensifies and automates dendrimer production providing strict control over dendrimer synthesis. This process control enables the production of higher generation dendrimers to produce novel materials at higher yields and lower costs. Specific unit operations are integrated into the fractories including by way of example and without limitation, microscale mixers, separators, heaters and valves. Implementation of a nanofractory within a polymer sheet architecture provides the added advantages of an economical pathway to "numbering up" through microlamination.

E. Micromixer

In spite of the low purity achievable via divergent synthesis of higher generation dendrimers, this approach is more amenable to scale-up than the convergent approach. Polyamidoamine (PAMAM) is probably the most studied dendrimer today. In 1985 and 1986, Tomalia et al. described the preparation of PAMAMs by the divergent approach. The synthesis involves in situ branch cell construction in step-wise, iterative stages around a desired core (e.g. ammonia or ethylenediamine) to produce defined core-shell structures. Each generation was synthesized through a reiterative two-step reaction sequences involving (1) exhaustive alkylation of primary amines (Michael-type addition) with methyl acrylate and (2) amidation of amplified ester groups with a large excess of ethylenediamine to produce primary amine terminal groups. The first reaction sequence on the exposed dendron creates G=0. Iteration of the alkylation/amidation sequence produces an amplification of terminal groups from 1 to 2 with in situ creation of a branch cell at the anchoring site of the dendron that constitutes G=1. Conventionally, in order to achieve a high degree of product purity, the potential synthetic problems associated with amine additions to esters, including lactam formation, retro-Michael reactions, incomplete addition, and intermolecular coupling, were minimized using excess diamine, maintaining moderate reaction temperatures, and avoiding aqueous solvents. A recent ESI-MS (Electrospray Ionization Mass Spectrometry) study on PAMAM at the $4^{th}$ generation indicated that the sample under analysis possessed purity no more than 8%.

Microreaction technology offers several new opportunities to suppress competing side reactions and maximize product purity. These include uniform and precise temperature control and low moisture permeability to avoid water content. Most importantly, the key is to increase the conversion rate of the alkylation/amidation reaction sequence through enhancement of effective collision between reactants. Thus, it is beneficial to create a microfluid (mixing of reactants at the molecular level) rather than a macrofluid (aggregates of separate reactants).

Mixing typically involves integration of one or more fluids into one phase and molecular diffusion is usually the final step in all mixing processes. A simple estimation shows that it will take five seconds to mix two contacting 100 µm thick aqueous laminar layers containing small molecules and would only take 50 milliseconds if the layers were 10 µm. The essence of mixing thus relies on the concept of volume division. One common approach to achieve volume division is creating a turbulent flow. It is difficult to achieve uniform mixing at the micrometer scale in a short time by traditional mixing apparatus, such as paddles or propellers in a reaction tank. Micromixers offer features which cannot be easily achieved by macroscopic devices, such as ultrafast mixing on microscale. For example, Bokenkamp et al. fabricated a micromixer as a quench-flow reactor to study fast reactions (millisecond time resolution).

Figure 17:
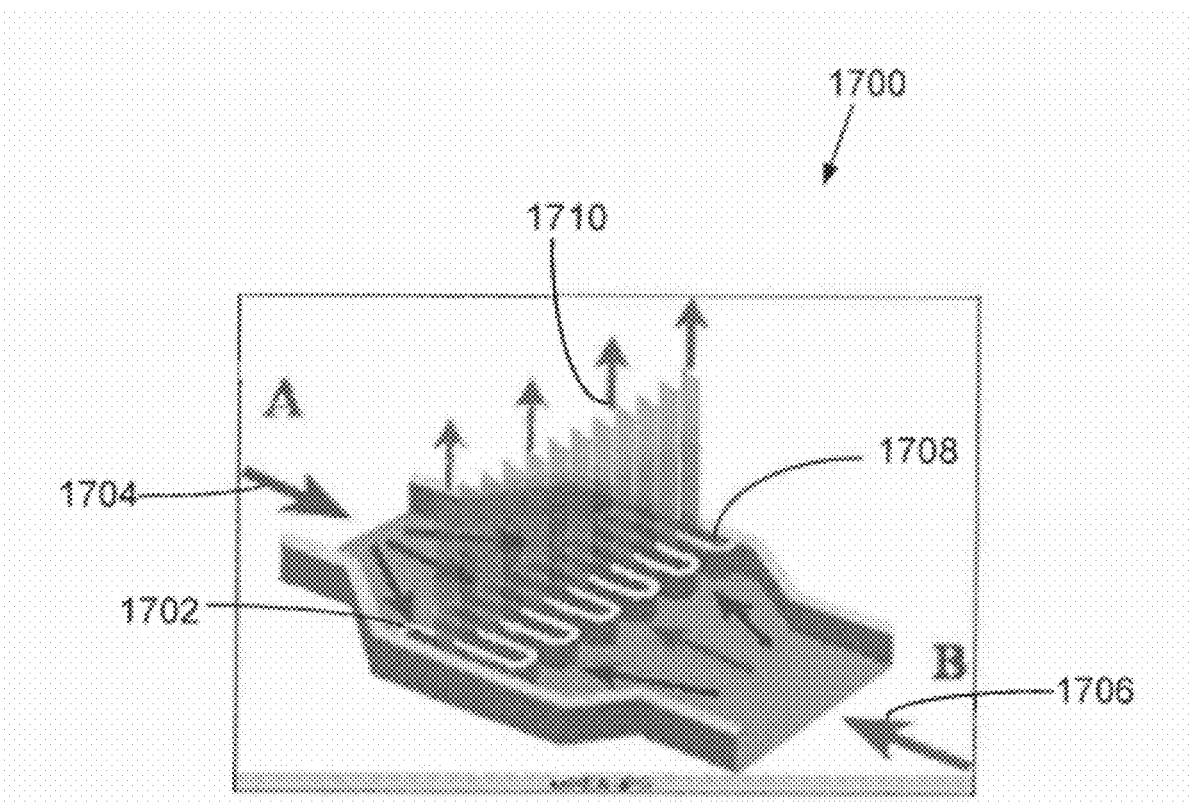
FIG. 17 is a schematic perspective diagram of one embodiment of an interdigital micromixer.
Figure 18A:
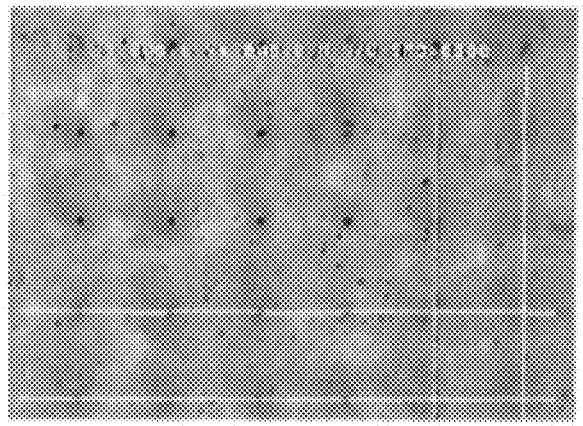
FIGS. 18A-18B are micrographs of (A) 75 µm thick laser-machined polyimide (200×) and (B) 15 µm thick micro-molded PDMS (500×) membranes with 5-8 µm pores on 100 µm spacing.
Figure 18B:
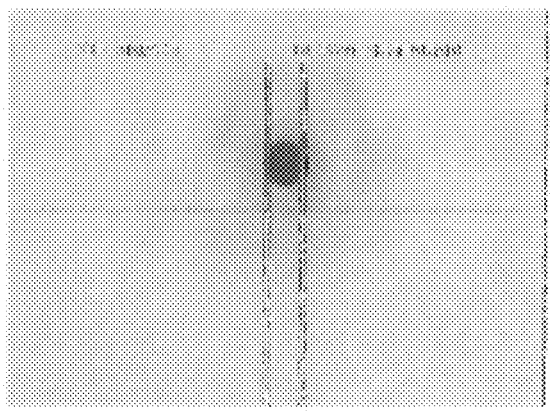

Alkylation and amidation reactions for dendrimer synthesis will be performed using different micromixers, such as an interdigital micromixer. A schematic perspective diagram of one embodiment of an interdigital micromixer 1700 is shown in FIG. 17. Fluids A and B to be mixed are introduced into the mixing element 1702 as two counter-flows 1704, 1706. Flows 1704 and 1706 enter interdigital channels (~20 to 50 µm) 1708, and split into many interpenetrated substreams 1710.

The substreams 1710 leave the interdigital channels 1708 perpendicular to the direction of the feed flows, initially with a multilayered structure. Fast mixing through diffusion soon follows due to the small thickness of the individual layer. Silicon-based interdigital type mixers described in the technical literature can be made using a polymeric microlamination architecture using replica molding/polymer embossing and various bonding strategies. Spacing between digits on the order of 20 μm can be achieved, which provides mixing times on the order of a few hundred milliseconds depending upon flow rates. This has been tested by generating cadmium sulfide (CdS) nanoparticle solution using a PDMS interdigital micromixer. Stable monodispersed CdS nanoparticle suspensions were produced even without adding stabilizers.

Micromixers can be engineered to control the orientation of higher generation dendrons upon mixing. Two types of micromixers are particularly promising. One is based on the collision of two high-energy substreams and the other is based on the injection of multiple microjets (or nanojets) into a mixing chamber. Membranes with straight-through pores down to 5 μm have been laser micromachined in 75 μm thick Kapton KJ and micromolded in 40 μm thick PDMS. Even at 100 μm spacing between pores at a mass flux of 0.5 g/min/$cm^2$, pressure drop across the membrane has been measured to be only a few ton.

Figure 19:
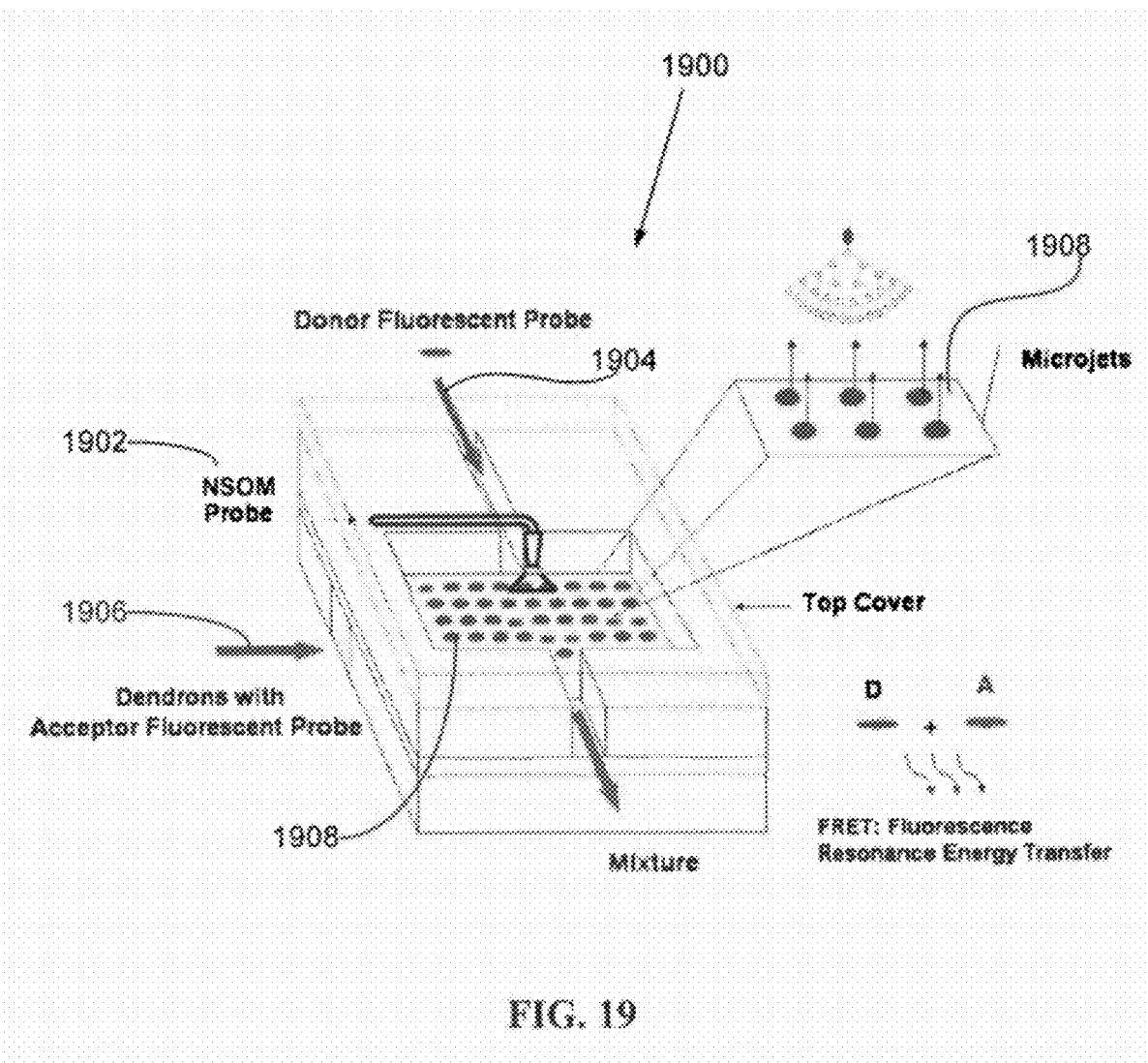
FIG. 19 is a schematic diagram of an exemplary analytical micromixer with a NSOM (Near-field optical microscopy) ear optical fiber probe.

FIG. 19 shows a schematic diagram of an exemplary analytical micromixer 1900 with a NSOM (Near-field optical microscopy) ear optical fiber probe 1902. Micromixer 1900 provides for flow 1904 and 1906 to plural microjets 1908. A resulting mixture stream 1910 flows from the microjets 1908. Other analytical micromixers based on different mixing principles will also be built and studied.

Location-specific production and immobilization of dendrimer-templated sorbents in-situ will be used in microfluidic devices for separations. This same method can be used to build nanopreparative separators in specific locations in the nanofractory. This recursive design will employ the dendrimer as a template in porous polymer sorbent synthesis. This new technology for the preparation of porous monolithic sorbents will provide enhanced control over surface chemistry and porosity, and enhance separations.

PDMS microchips provide useful surface chemistry for ligand attachment if first exposed to an oxygen plasma. Such exposure introduces silanol groups that are useful to bond adjacent device components and to attach polymers and other ligands to the surface in the flow conduit. In the former role the silanols condense with complementary functional groups on other surfaces (such as quartz, glass, other PDMS components, etc.) to yield a stable, leak-free seal. In the latter role the activation chemistries described above are available for use in coupling primary-amine-containing ligands. In the event that an insufficient surface coverage of silanols exist for effective immobilization of sorbents, $SiO_2$ doped PDMS matrices and matrices incorporating both PDMS and —$NH_2$ or —OH terminated PDMS may be employed. Several other reasonable approaches to surface activation and ligand immobilization exist.

F. Integrating Microscale Separations Devices into the Nanofractory

Although others have demonstrated integrated systems for analysis—systems incorporating multiple mixing, separations, injection, and detection steps—no example apparently is yet known in the literature for a highly integrated manufacturing microdevice. Such a device likely would include reagent delivery, mixing, heating, reaction, purification, isolation, and transport elements into a single device. Further, these operations may need to be iterated multiple times to yield a complex product. The separative components described herein, capable of extractions and chromatography, shall be integrated into the nanofractory architecture.

Prior efforts have shown the ability to integrate injection systems with multiple separators, mixers and separators or reactors and separators on a single chip. Also, efforts have been made to integrate cell lysis, PCR amplification, separation and detection on one chip for DNA analysis. These integrations were all performed on a single glass chip using a cruciform channel design. Surface area to volume (SAV) ratios for these designs were on the order of 0.005 $mm^2/mm^3$.

VI. Fractal Microchannels

Figure 20A:
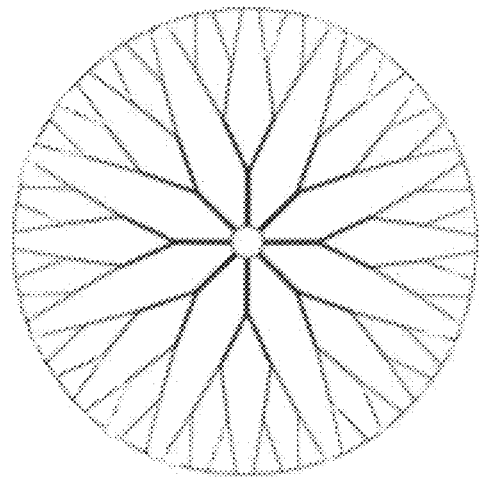
FIGS. 20A and 20B illustrate one approach to fabricating a "nanofractory": (a) an in-line fractal design for compact production of dendrimers (geometry based on the work of Pence) and b) a close up of one of the vertices in the fractal device with integrated micromixer, heater and separator.
Figure 20B:
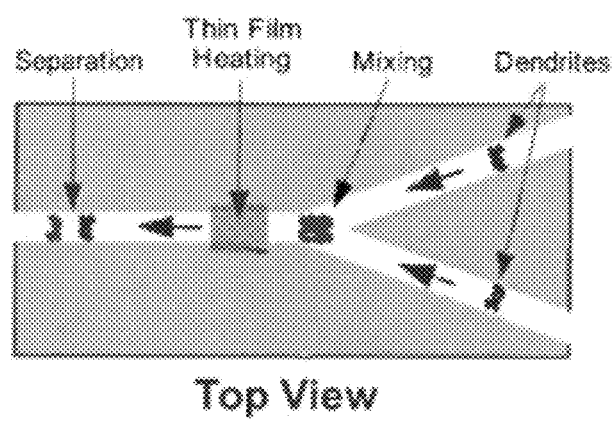
Figure 21A:
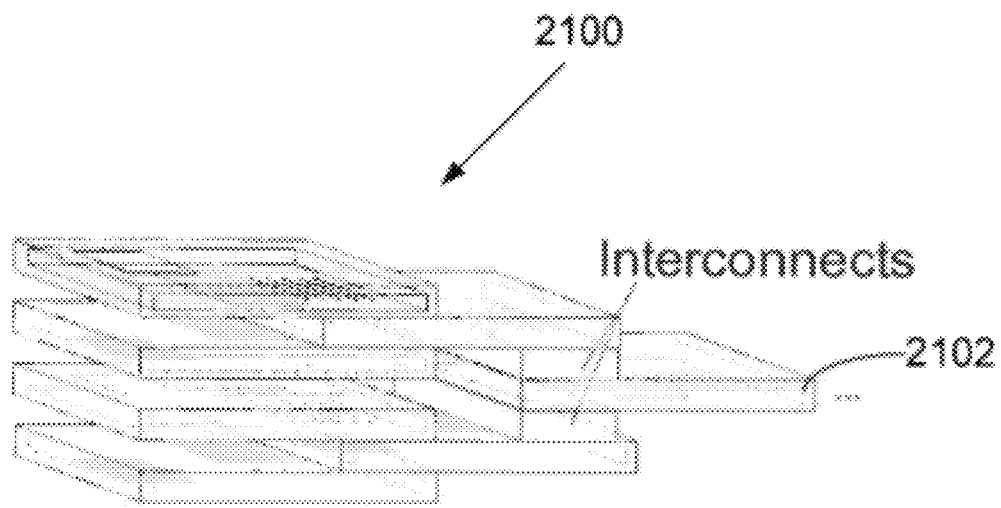
FIGS. 21A-21B illustrate an alternative modular approach to nanofactory development.

The large, fractal sequence of reactions necessary for convergent dendrimer production lends itself to the implementation of a fractal nanofactory, or "nanofractory" illustrated by FIGS. 20 and 21.

The nanofractory actually mimics the geometry of the dendritic molecule it produces. Fractal microchannels have been proposed in heat transfer applications to lower pumping powers and improve thermal distribution on heat transfer surfaces. These benefits derive mainly from the minimization of microchannel flow path lengths and the continual disruption of hydrodynamic and thermal boundary layers caused by the regular bifurcation of the flow. The space efficiency of fractal networks is used to improve the channel and unit operation packing density, thereby making the nanofractory compact. Chamber dimensions for the disclosed embodiment will be on the order of 50 to 100 μm dictated largely by mixing times, flow rates, residence times, etc.

Figure 21B:
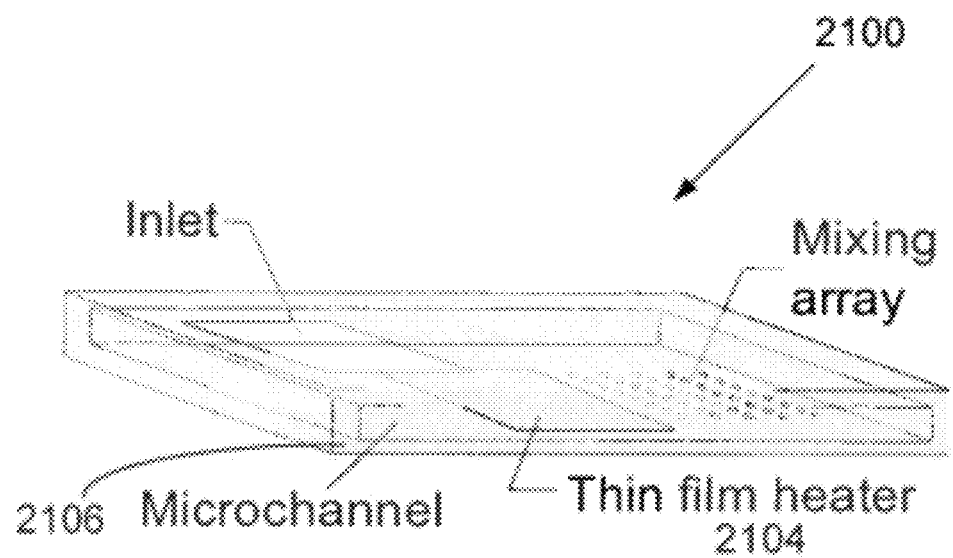

An alternate approach to nanofractory development is shown in FIG. 21. This modular approach could be used for both divergent and convergent synthesis. Microarrays 2100 may include plural layers 2102. The array 2100 of FIG. 21B includes thin film heaters 2104 adjacent a microchannel and a mixing array 2106 to support material synthesis. Thin films 2104 are evaporated onto substrates and integrated into microchannels using various bonding methods.

Figure 27:
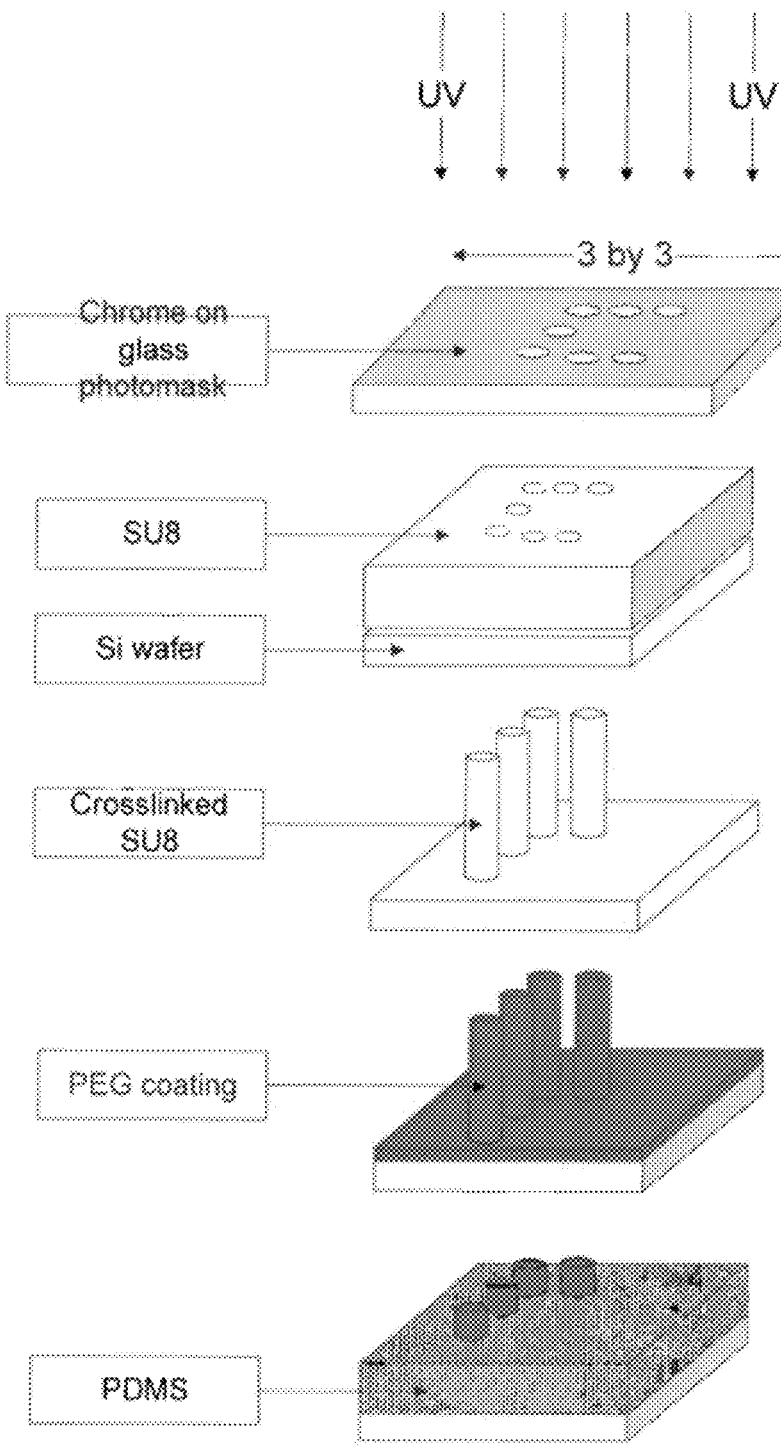
FIG. 27 is a schematic drawing illustrating one embodiment of a method for making a contactor membrane by micromolding techniques.

Modular microchannel packages will be developed using a Si bulk micromachining/anodic bonding architecture or soft lithography techniques. FIG. 27 of the priority provisional application illustrates a single cruciform set of channels made by soft lithography with a cross-section nominally 40 μm square that was used for dendrimer templating of a chromatographic channel. Further, PDMS substrates may be used as mandrels for replica molding polyurethane (cross-linked) or vacuum casting polyethylene (thermoplastic) devices in modest volumes. A replicated substrate with nominally 100 μm bifurcated flow paths from a chemically-etched 304 stainless steel substrate also has been made. The replica is low-density polyethylene (LDPE) and was reproduced to a dimensional accuracy of 5%.

Strategies for reagent injection and extraction will be based on mechanical valves developed by Thorsen, et al., which have been implemented in high densities (i.e. more than 3500 valves in 625 $mm^2$) in PDMS architectures. Based on this, it is expected that mechanical injection and extraction will be more space efficient than other chemical means of injection (via electrokinetic pumping) or extraction (via liquid-liquid extraction), which may require channel lengths on the order of tens of mm. Second, while the level of valve integration reported in the literature is currently impressive, the surface-area-to-volume (SAV) ratio for these devices is still only around 0.1 $mm^2/mm^3$ due to the poor modulus of the packaging material (PDMS) requiring even single layer chips to be several mm thick. This ratio could be significantly improved by packaging these systems with stiffer polymers. Furthermore, packaging of these systems in polymers with lower gas permeabilities will help to eliminate the problems of bubble formation within the channels.

Figure 22:
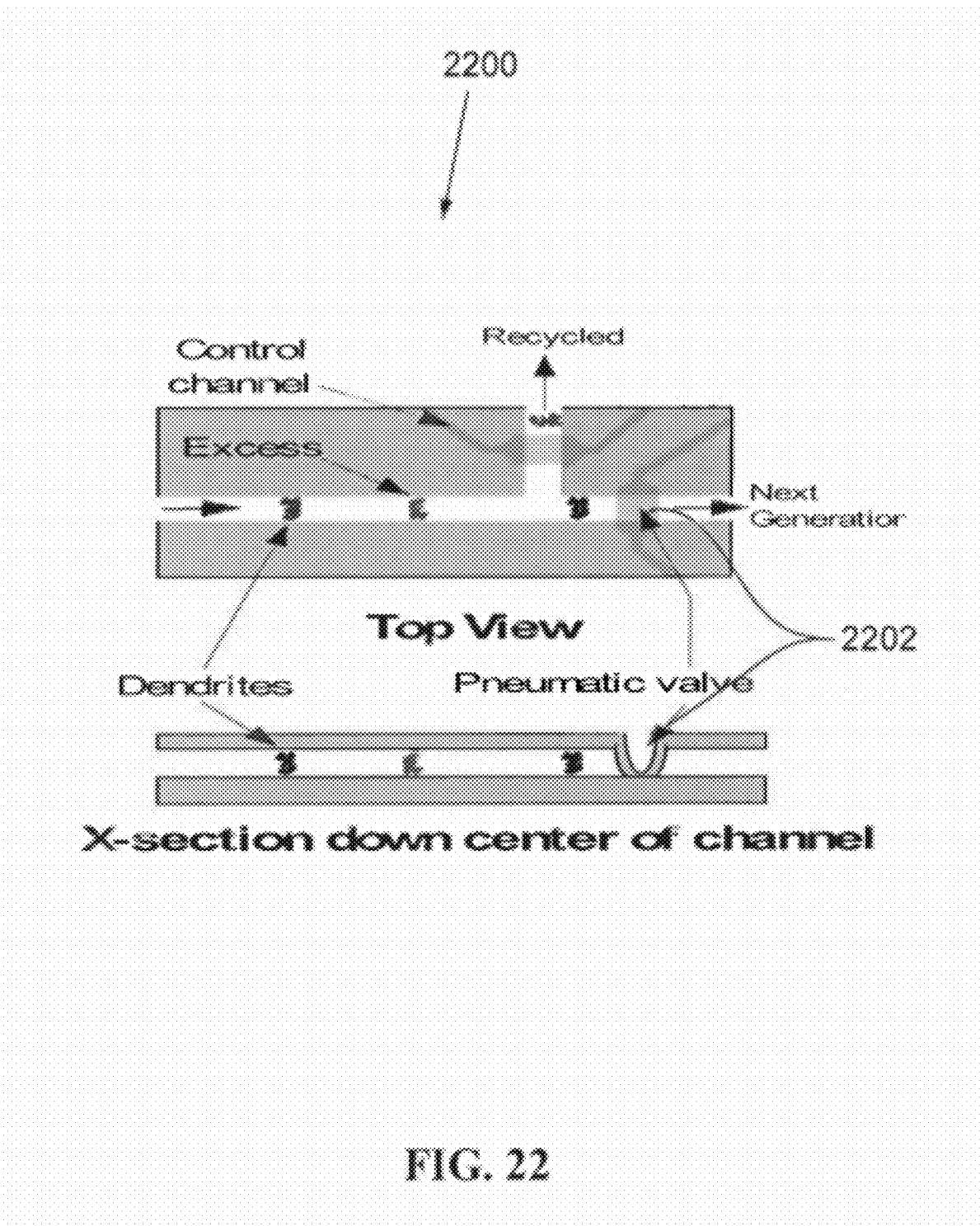
FIG. 22 illustrates using mechanical valves for dendron extraction.

FIG. 22 illustrates how mechanical valves like those developed by Thorsen, et al., will be used in dendron extraction. The array 2200 includes fast acting and leak tight valves 2202 having a low pressure drop and small footprint. Thorsen, et al., demonstrated the large-scale integration (LSI) of pneumatically-actuated microvalves using multi-layer soft lithography techniques. The pneumatic and hydraulic valves in the LSI concept by Thorsen, et al., are driven by benchtop compressors and pumps, which require bulky pneumatic and hydraulic control channels. Pneumatic actuation of the valves could result in gas contamination of the reaction stream due to the gas permeability of the PDMS. In addition, the distribution system for pneumatic actuation is bulky and not desirable within high component density applications such as the nanofractory. Electrically-actuated microvalves capable of being integrated within a nanofractory architecture can be made by combining a thin film heater with a material having a large thermal expansion. Paraffin waxes possess a very large thermal expansion (10-35%) with the potential to deliver very large pressures (500 Mpa) and have been demonstrated in surface micromachined and polymer embossing architectures. Other electrical actuation possibilities include electrostrictive polymers which would actuate when placed between two static electrodes. In this way, thin film electrical traces will be used to replace the pneumatic or hydraulic control networks in Thorsen's work. PDMS is known to be highly gas permeable, which results in the evaporation of liquids and the formation of bubbles in microchannels. Bubbles on the order of 1 mm in diameter have been observed to form within 24 hours, which, in 100-micron channels, causes vapor-lock and hinders reactions. This may be handled by using conformal sealing, which will make the removal of air bubbles possible. Additional efforts will be needed to package PDMS valves within stiff, low gas permeable polymers.

Figure 23A:
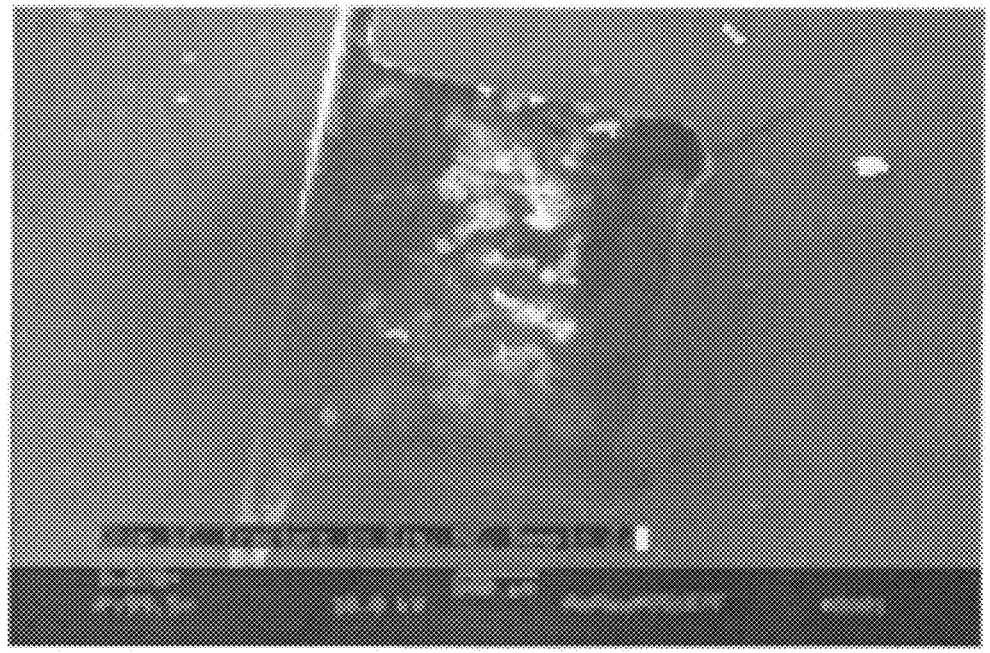
FIGS. 23A-23B are photomicrographs illustrating monolithic sorbent materials produced in PDMS microchannels with sufficient anchoring to yield a useful device for separations.
Figure 23B:
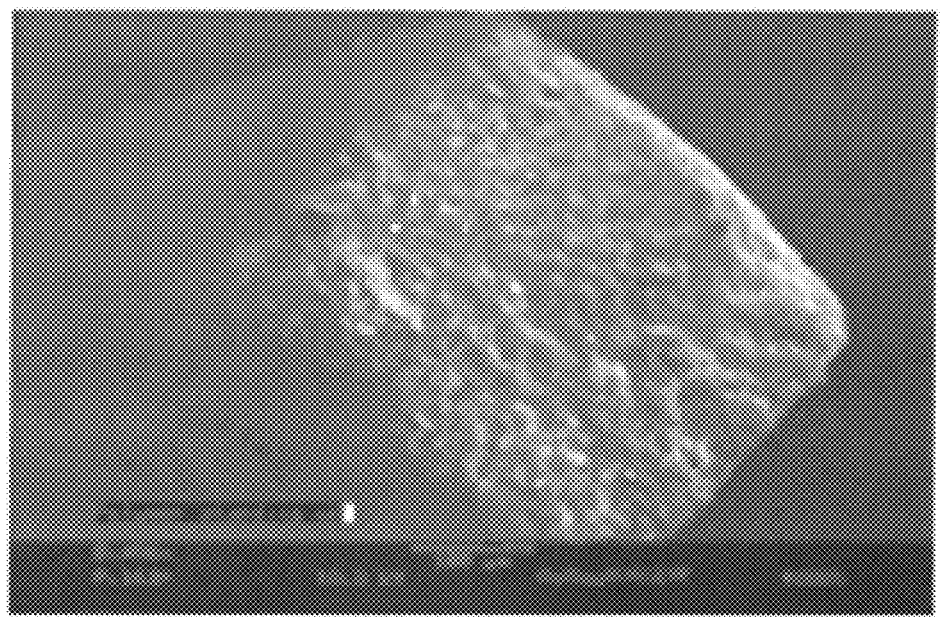

Using the methods described herein, monolithic sorbent materials have been produced in PDMS microchannels with sufficient anchoring to yield a useful device for separations. Channel cross-sections are shown in FIG. 23A-B.

The porosity of the polymeric stationary phase in monolithic columns is usually dictated by the nature and amount of the porogenic solvent employed. Aside from affecting porosity, adjustments of the amount and nature of the porogenic solvent(s), alter other properties such as the surface area, nature and swelling properties of the resulting monoliths. Recently, Chirica and Remcho described a new synthetic method for preparing monoliths with porosity dictated by the size of spherical silica particle templates. In addition to tailoring the pore size, this method offers the ability to influence the surface characteristics of the finished polymer by employing silica beads with specific surface chemistry.

Dendrimers also can be used to generate uniform pore structures. Polyamidoamine (PAMAM) dendrimers represent one class of useful macromolecules. The macromolecules are incorporated into a solution of functionalized monomers, cross-linker, solvent, and polymerization initiator. Thermal or photo-initiation of polymerization, which can be localized in a microscale device by (1) localized heating with an in-situ micro heater, or (2) by use of a photomask and exposure to a UV source, results in polymer production. This is followed by the removal of solvent and dendrimers, which yields a continuous rod of polymer with uniform porosity and dendrimer-influenced surface character.

Figure 24A:
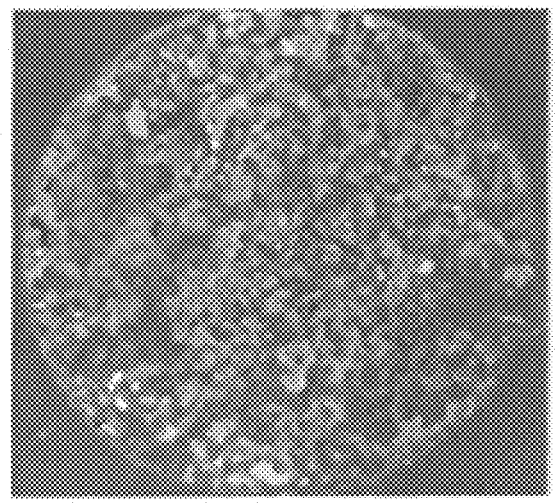
FIGS. 24A-24C are SEM images of a polymer made using the embodiments of the device described herein.
Figure 24B:
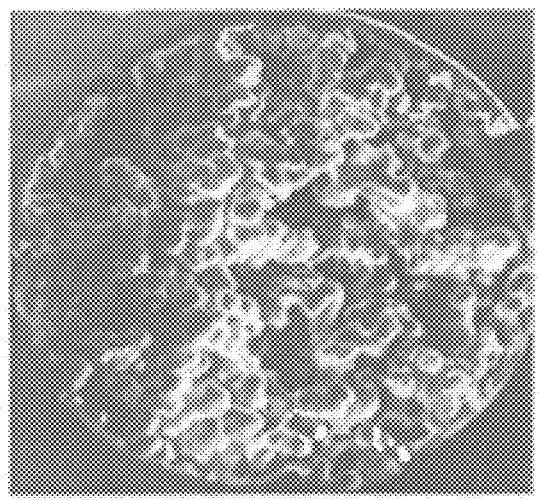
Figure 24C:
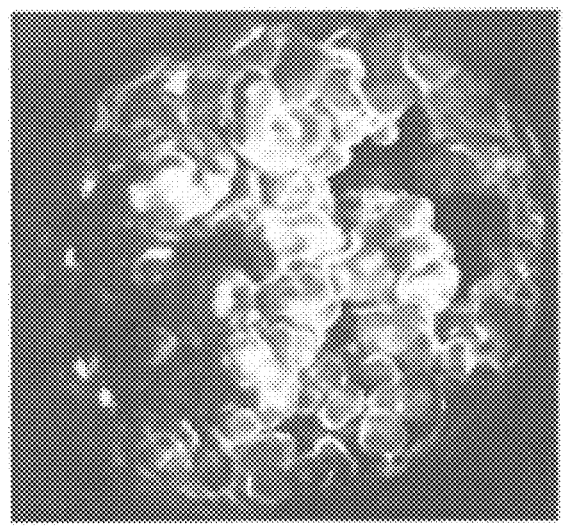

In one embodiment of this method, azobisisobutyronitrile (AIBN, 1 wt % with respect to the monomers) was dissolved in a monomer mixture consisting of 40% ethyleneglycol dimethacrylate (EDMA), 59.7% butylmethacrylate (BMA) and 0.3% 2-methyl-1-propane sulfonic acid (AMPS). A porogenic solvent, methanol, was slowly admixed with the monomers in a 2:3 (v/v) ratio with the goal of producing interconnecting micropores in the monolith. One ml aliquots of this mixture were added to several vials containing specific amounts of Starburst (PAMAM) dendrimer. The dendrimer, commercially available as a 10% solution in methanol, was used after the removal of methanol by vacuum distillation. After addition of the monomer solution, the homogeneous mixtures were purged with nitrogen for 10 minutes. A fused silica capillary was filled with the polymerization mixture using a 100 ml syringe. Both ends of the capillary were sealed with rubber septa, and the column was submerged in a 60° C. bath for 20 hours. Using a syringe pump, the resulting monolith was washed with the mobile phase to flush out the residual reagents, dendrimers and methanol. An SEM image (cross-section) of the resulting polymer is shown in FIG. 24A-C.

Liquid-Gas Contactor

Figure 25:
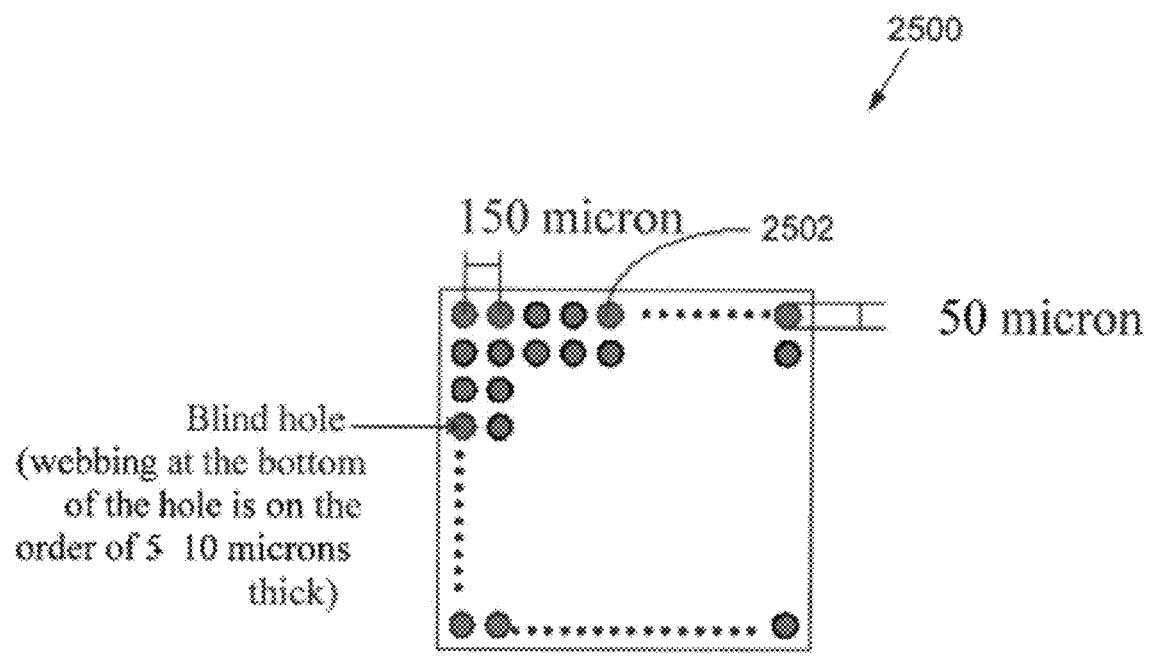
FIG. 25 is a schematic plan view of a gas-liquid contactor membrane.

Microchannels operatively associated with membranes can be used for a variety of applications. Another example concerns a liquid-gas contactor that can be used to facilitate gas absorption in the liquid. FIG. 25 illustrates one embodiment of liquid-gas contactor membrane 2500 that can be used to flow a liquid adjacent one surface of the membrane in a microchannel, and a gas adjacent a second surface of the membrane in another microchannel. The liquid/gas contactor membrane 2500 illustrated in FIG. 25 has a thickness of several hundred microns. This provides ribbing for stiffening the membrane, which will be positioned between gas and liquid flowing microchannels. Thin webbing in the bottom, on the order of 5-10 microns thick, is provided in the membrane 2500. A laser is used to ablate small apertures (1-2 micron diameter) 2502 in the webbing. Apertures 2502 having a diameter of about 50 microns and a separation distance of about 150 microns are illustrated in FIG. 25. This allows gas/liquid contact without breakthrough of the liquid into the gas. Because of the contact, gas, such as oxygen, can be absorbed into the liquid.

Contactor Membranes in Absorption/Desorption Cycle Micro-Scale Heat Pumps

Figure 26:
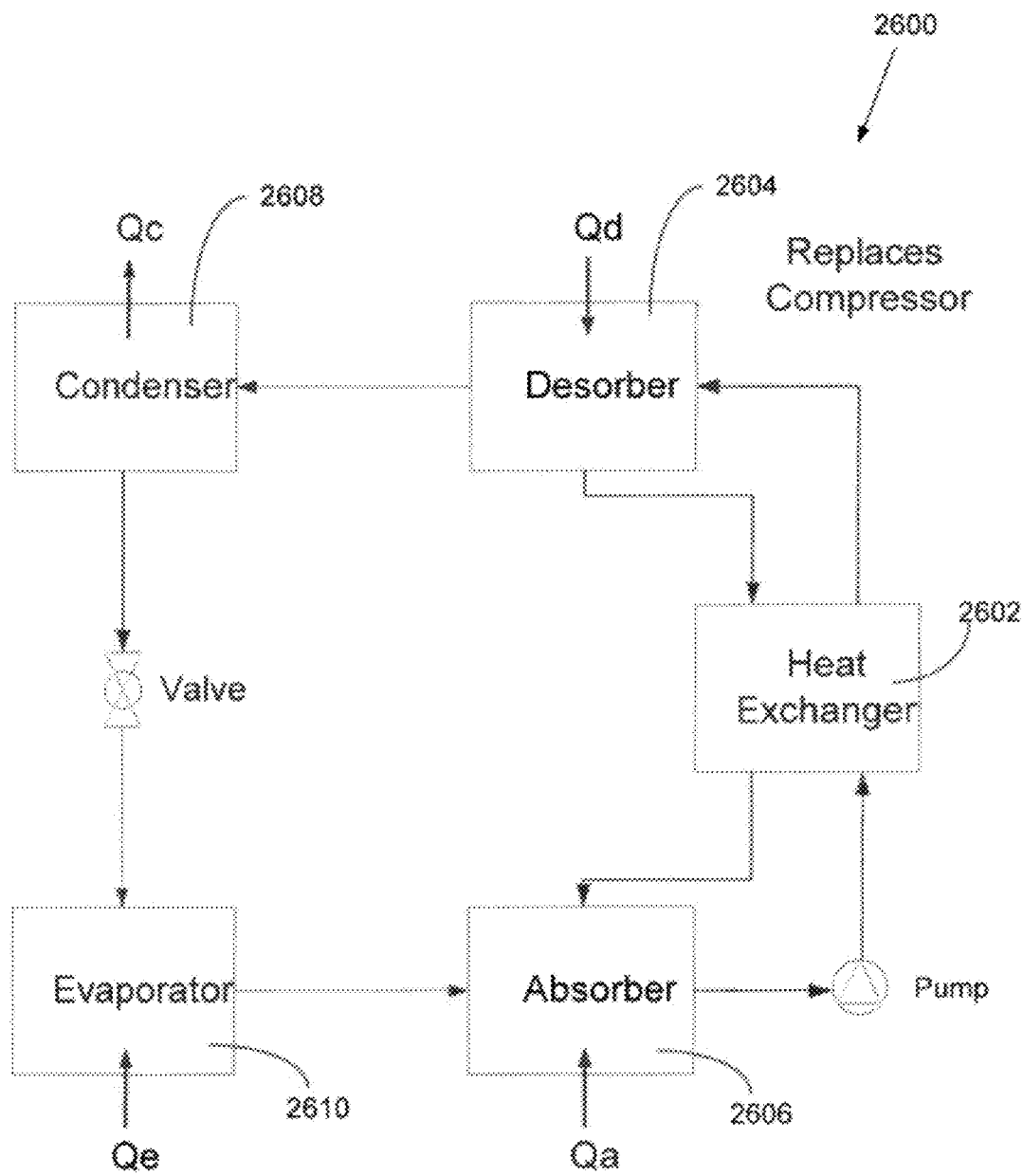
FIG. 26 is a schematic drawing illustrating the basic components of a heat exchanging system.

Another potential application of microchannels operatively associated with membranes is a contactor membrane for use in a micro-scale heat pump using absorption/desorption cycles. One embodiment of a heat pump is illustrated in FIG. 32 of the priority provisional application. FIG. 26 provides a schematic drawing illustrating the basic components of a heat exchanging system 2600. The illustrated heat exchanging system 2600 includes heat exchanger 2602, a desorber 2604, an adsorber 2606, a condenser 2608 and an evaporator 2610. Contactors useful for heat exchanger applications have a number of desirable physical characteristics, including having a sufficient stiffness for the application, a thickness of from about 50 to about 150 microns, a pore size of from about 1 to about 10 microns, a high break through pressure, which is the pressure at which solution will pass through the contactor, a high permeability (mass flux/pressure drop), and a low pressure drop (the minimum refrigerant vapor pressure for driving the absorption/desorption process).

Suitable contactor membranes can be made by laser micromachining. The method involved first selecting a suitable material, examples of which include polyimide and polycarbonate. A membrane was made from such materials by laser micromachining using a 266 nm Nd:YAG laser. Contactors also can be made by micromolding the membrane. This involved using a photoresist, such as SU8 2050, a photomask having appropriate pore sizes, such as a chrome on glass photomask having 5 micron pores, a substrate, such as a silicon wafer substrate, and polymeric materials, such as PDMS, PEG, etc. FIG. 27 schematically illustrates the method for making the contactor by micromolding techniques.

Figure 28:
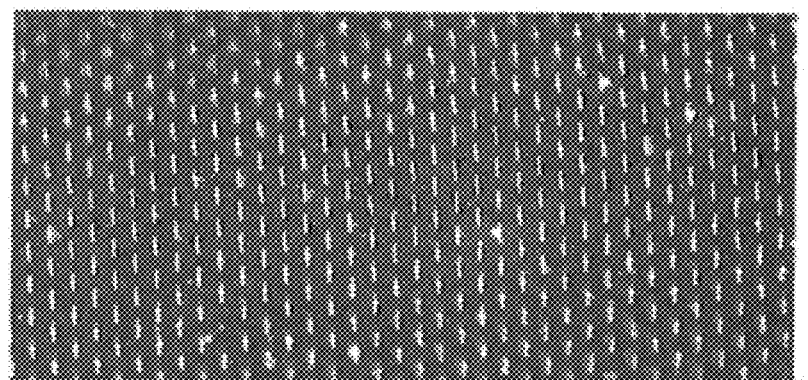
FIGS. 28-30B illustrate the results obtained by micromolding contactors.
Figure 29:
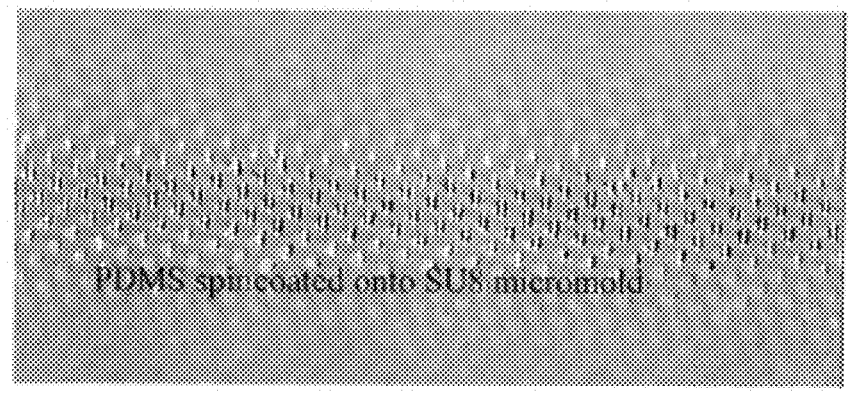
Figure 30A:
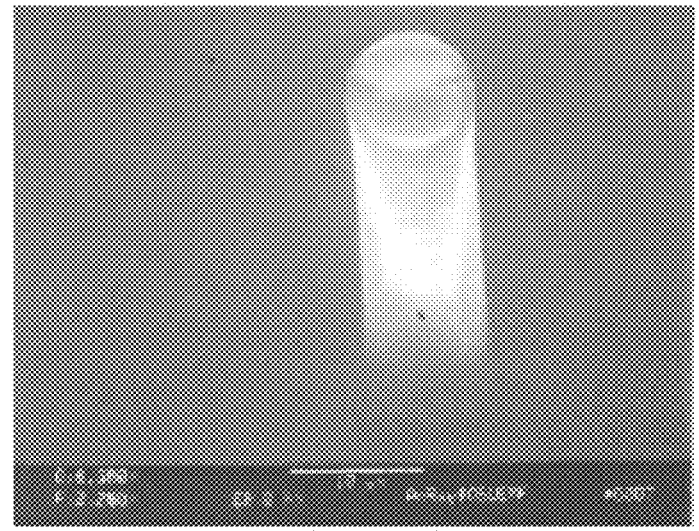
Figure 30B:
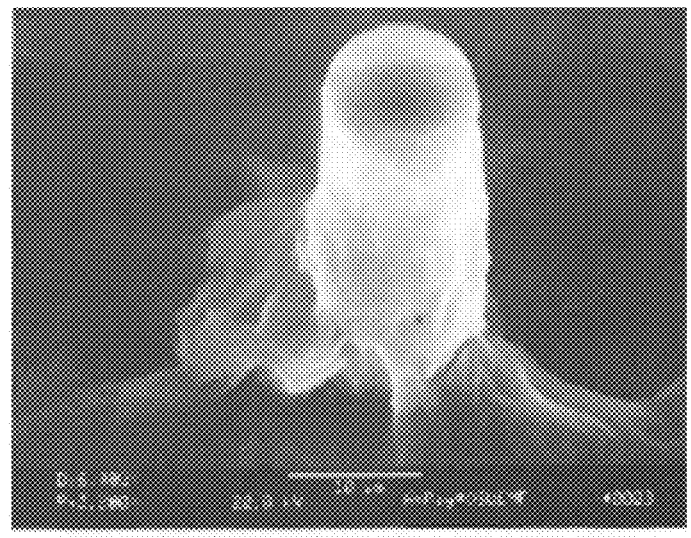

FIGS. 28 and 29 illustrate the results obtained by micromolding contactors. Laser micromachined and micromolded membranes with straight-through pores have been fabricated according to the methods described herein. The morphologies of a engineered straight-through membrane have better permeability then conventional membranes. The engineered membranes show at least 10 times more mass flux then conventional membranes in a normalized permeability plot.

The present invention has been disclosed with reference to particular embodiments that exemplify the scope of the invention. A person of ordinary skill in the art will appreciate that the scope of the invention can vary from that disclosed herein with reference to these particular embodiments.

We claim:

1. A dialyzer, comprising:
   a semipermeable dialyzer membrane;
   a microchannel fluidic device fluidly associated with the membrane to provide a blood flow adjacent to and on one side of the membrane through a first plurality of microchannels having a first end, a second end and plural parallel channels extending between the first and second ends, and a dialysate flow adjacent to and on a second side of the membrane through a second plurality of microchannels arranged in a counterflow manner with the first plurality of microchannels, the second plurality of microchannels having a first end, a second end and plural parallel channels extending between the first and second ends, wherein the first end of the second plurality of microchannels corresponds to the second end of the first plurality of microchannels;
   a microscale heat exchanger operatively associated with the microchannels;
   a first fluid inlet fluidly coupled to the first plurality of microchannels for delivering blood to the first plurality of microchannels;
   a second fluid inlet fluidly coupled to the second plurality of microchannels for delivering dialysate to the second plurality of microchannels;
   a first plurality of posts uniformly distributed across the first end of the first plurality of microchannels defining a header located adjacent the microchannels for distributing fluid to the first plurality of microchannels to distribute blood flow substantially equally among the first plurality of microchannels; and
   a second plurality of posts uniformly distributed across the first end of the second plurality of microchannels defining a header located adjacent the microchannels for distributing dialysate flow substantially equally among the second plurality of microchannels.

2. A dialysis method, comprising:
   flowing blood from a patient requiring dialysis to a dialyzer comprising (a) a semipermeable dialyzer membrane, (b) a microchannel fluidic device fluidly associated with the membrane to provide a blood flow adjacent to and on one side of the membrane through a first plurality of microchannels having a first end, a second end and plural parallel channels extending between the first and second ends, and a dialysate flow adjacent to and on a second side of the membrane through a second plurality of microchannels, the second plurality of microchannels having a first end, a second end and plural parallel channels extending between the first and second ends, (c) a first fluid inlet fluidly coupled to the first plurality of microchannels for delivering blood to the first plurality of microchannels, (d) a second fluid inlet fluidly coupled to the second plurality of microchannels for delivering dialysate to the second plurality of microchannels, (e) a first plurality of posts that define a header located adjacent the microchannels for distributing blood flow substantially equally among the first plurality of microchannels, (f) a second plurality of posts that define a header located adjacent the microchannels for distributing dialysate flow substantially equally among the second plurality of microchannels, and (g) a heat exchanger operatively associated with the microchannels; and
   flowing dialysate to the second single-fluid inlet.

* * * * *